United States Patent
Ozaki et al.

(10) Patent No.: US 7,462,324 B2
(45) Date of Patent: Dec. 9, 2008

(54) MEASUREMENT DEVICE AND METHOD FOR MEASURING ELECTRIC SIGNAL FROM BIOLOGICAL SAMPLE

(75) Inventors: Nobuhiko Ozaki, Ikoma (JP); Hiroaki Oka, Hirakata (JP); Hirokazu Sugihara, Katano (JP)

(73) Assignee: Panasonic Corporation, Osaka (JP)

( * ) Notice: Subject to any disclaimer, the term of this patent is extended or adjusted under 35 U.S.C. 154(b) by 1034 days.

(21) Appl. No.: 10/495,621

(22) PCT Filed: Nov. 19, 2002

(86) PCT No.: PCT/JP02/12085

§ 371 (c)(1),
(2), (4) Date: May 14, 2004

(87) PCT Pub. No.: WO03/044512

PCT Pub. Date: May 5, 2003

(65) Prior Publication Data
US 2005/0004442 A1    Jan. 6, 2005

(30) Foreign Application Priority Data
Nov. 19, 2002   (JP) .............................. 2001-353829

(51) Int. Cl.
 G01N 27/00   (2006.01)
 G01N 15/06   (2006.01)
 G01N 33/53   (2006.01)
 G01N 25/18   (2006.01)

(52) U.S. Cl. .................... 422/82.01; 422/50; 422/68.1; 422/82.02; 422/82.03; 435/6; 435/7.1; 436/149; 436/150

(58) Field of Classification Search ................. None
See application file for complete search history.

(56) References Cited

U.S. PATENT DOCUMENTS
6,068,818 A  *  5/2000  Ackley et al. ................. 422/50
2001/0005774 A1   6/2001  Kato et al.

FOREIGN PATENT DOCUMENTS
JP     6-201638    7/1994
JP     9-211010    8/1997

(Continued)

*Primary Examiner*—Jill Warden
*Assistant Examiner*—Neil Turk
(74) *Attorney, Agent, or Firm*—McDermott Will & Emery LLP

(57) ABSTRACT

A measurement device 10 includes a measurement cell 11. The measurement cell 11 includes a substrates 17 and a substrate 16 formed on the substrate 17. The substrates 16 and 17 are bonded to each other. Thus, a flow pass 9 is formed in the measurement cell 11. As shown in FIG. 3, on the substrate 17 of the measurement cell 11, provided are a concave well 19, a protruding microelectrode 1 connected to a terminal 4a and formed on a side wall surface of the well 19, communicating tubes 15a and 15b connected to both of side surfaces of the well 19 (i.e., the flow pass 9) to face to each other, resistance baths 6a and 6b connected to the communicating tubes 15a and 15b, thin film resistors 3a and 3b arranged in the resistance baths 6a and 6b, and a reference electrode 2 connected to a terminal 4b.

18 Claims, 13 Drawing Sheets

FOREIGN PATENT DOCUMENTS

| | | |
|---|---|---|
| JP | 9-211010 A | 8/1997 |
| JP | 9-289886 | 11/1997 |
| JP | 9-289886 A | 11/1997 |
| JP | 2001078748 A | 9/1999 |
| JP | 11-299496 | 11/1999 |
| JP | 11-299496 A | 11/1999 |
| JP | 2001-183329 | 7/2001 |
| JP | 2001-183329 A | 7/2001 |
| JP | 2001-193329 | 7/2001 |
| WO | WO 99/08095 | 2/1999 |

* cited by examiner

MEASUREMENT DEVICE AND METHOD FOR MEASURING ELECTRIC SIGNAL FROM BIOLOGICAL SAMPLE

TECHNICAL FIELD

The present invention relates to a measurement device for electrophysiological evaluation of a biological sample.

BACKGROUND ART

Conventionally, in chemical screening using a biological sample (represented by a cell), the action of a cell is monitored by fluorochrome method or a micropipette electrode method to evaluate the action and effect of a drug for the cell.

Fluorochrome methods are methods for optically measuring, using fluorochromes which specifically react with various ion concentrations and a membrane-potential-sensitive fluorochrome, the action of a cell which is influenced by a drug, i.e., the degree of change in fluorescence of the cell according to changes in the membrane potential and ion concentration of the cell. In fluorochrome methods, the step of staining a cell with a dye is necessary. Therefore, influence of a dye to a cell can not be eliminated. Moreover, in fluorochrome methods, fluorescence from a fluorochrome is weakened with time, so that detection accuracy becomes poor. This is a weak point of fluorochrome methods.

On the other hand, micropipette electrode methods are of a method for directly measuring an electrical action of a cell, such as an intracellular potential, a current flowing through an ion channel existing in a cell membrane, a current flowing through a channel activated by a drug receptor. Therefore, with the micropipette electrode method, more detail and wider range of information about the action of a cell which is influenced by a drug can be obtained. The micropipette electrode method is a very useful method for obtaining information about the action of a cell.

In general, in an intracellular potential recording method that is one of micropipette electrode methods, a micropipette formed by stretching thermally-melt quartz glass or borosilicate glass so as to have a submicron tip diameter is inserted into a cell. Moreover, in a patch clamp method that is one of micropipette electrode methods, to locally measure a very small region of about 0.1-20 micron in the cell, a micropipette is pressed against a cell membrane so that the micropipette and the membrane are attached to each other at a predetermined angle.

Problems to be Solved

However, in a known micropipette electrode method, a technician operates a micropipette, relying on a micrograph, to insert a micropipette into a cell fixed onto a substrate, or attach a micropipette to the cell. Therefore, a highly accurate micropipette position controller is needed, and furthermore, a skill to insert a micropipette into a cell or attach a micropipette to a cell is needed.

Accordingly, the micropipette electrode methods are not suitable as a technique for screening a large amount of compounds as candidates for drugs at high speed.

In Japanese Laid-Open Patent Publication 9-289886, a cell membrane potential detector for use in a micropipette electrode method is disclosed. The cell membrane potential detector includes a protruding electrode for cell insertion, which is provided on a bottom face of a dish having a plurality of with bottom holes and serves as a micropipette, and a reference electrode provided in a side surface of each of the with bottom holes.

The cell membrane potential detector disclosed in the publication does not include means for accurately leading a cell to the protruding electrode. Therefore, a skill of a technician is needed to lead a cell to a protruding electrode.

In view of the above-described problems, the present invention has been devised to provide a measurement device which allows electrophysiological measurement of a biological sample to be performed in a simple, accurate, high-speed and automatic manner.

DISCLOSURE OF INVENTION

A measurement device according to the present invention is a measurement device for measuring an electric signal from a biological sample and includes: a flow pass extending in a first direction; a pair of introduction orifices connected to both ends of the flow pass, respectively; a concave well formed in the flow pass; a reference electrode formed in the flow pass; at least a microelectrode formed in the well; a first communicating tube connected to the well and extending in a second direction different from the first direction; a second communicating tube connected to other part of the well than part of the well to which the first communicating tube is connected and extending in a third direction different from the first and second directions; first and second resistance baths connected to the first and second communicating tubes, respectively; and first and second resistors arranged in the first and second communicating tubes, respectively, or the first and second resistance baths, respectively.

In the measurement device of the present invention, when a current is applied to the first and second resistors, the first and second resistors consume electric energy and generate heat. The measurement device is used with the flow pass filled with an electrolyte solution and a medium capable of changing an interfacial tension with the electrolyte solution in each of the first and second resistance baths added thereto, and currents having different current values are applied to the resistors, respectively. Thus, the interfacial tension between the medium shut into each of the first and second resistance baths and the electrolyte solution in each of the first and second communicating tubes is decreased in proportion to the quantity of heat generated by the resistors. As a result, the electrolyte solution in the first and second communicating tubes moves from the resistance bath of a higher temperature to the resistance bath of a lower temperature. This causes a local flow of the electrolyte solution in the well. By using the local flow, a biological sample is accurately and quickly led to the microelectrode, and then electrophysiological measurement of the biological sample can be performed. Therefore, with the measurement device of the present invention, a highly accurate position controller, which has been required in a known device of this type, and a skilled operation are no longer necessary.

It is preferable that the first and second communicating tubes are arranged so as to have line symmetry with respect to the flow pass.

Thus, calculation of the direction in which and the speed at which the biological sample is led by the local flow of the electrolyte solution in each of the first and second communicating tubes can be simplified very much.

It is preferable that said at least a microelectrode includes a protruding end portion.

Thus, the microelectrode can be inserted into the biological sample.

It is preferable that the first and second communicating tubes are arranged so that a straight line extending along the first communicating tube and a straight line extending along the second communicating tube intersect with each other toward said at least a microelectrode.

Thus, the local flow of the electrolyte solution in the well can be generated toward the microelectrode.

Said at least a microelectrode may be provided plural in number.

Thus, a plurality of biological samples can be fixed to the plurality of microelectrodes, respectively, so that all of the biological samples can be measured at the same time or each of the biological samples can be separately measured.

It is preferable that a surface area of the reference electrode is larger than a total surface area of the plurality of microelectrodes.

Thus, measurement stability against disturbances such as a solution flow can be improved.

The measurement device of the present invention may further include: a first substrate; and a second substrate formed on the first substrate, and have a structure in which the first substrate includes the well, the reference electrode, the microelectrode, the first and second communicating tubes, the first and second resistance baths, and the first and second resistors, and the second substrate includes a concave portion which serves as the flow pass when the second substrate is provided on the first substrate and extends in the first direction and cavities which serve as the pair of introduction orifices when the second substrate is provided on the first substrate and are formed in both ends of the concave portion, respectively.

It is preferable that the second substrate is formed of a transparent material.

Thus, the flow pass can be observed from the outside.

It is preferable that the second substrate is formed of a semiconductor device.

Thus, the first and second resistance baths and the first and second communicating tubes can be formed using a semiconductor fabrication technique known by a person skilled in the art. Specifically, if wet etching is used, by taking advantage of plane-directional selectivity, the first and second resistance baths and the first and second communicating tubes can be formed with high accuracy.

It is preferable that a volume of the first communicating tube is smaller than one fifth of a volume of the first resistance bath and a volume of the second communicating tube is smaller than one fifth of a volume of the second resistance bath.

Thus, by appropriately adjusting the interfacial tension in each of the first and second resistance baths, the location of an interface of the electrolyte solution can be controlled in a simple manner so that the interface is located in a desired position in each of the first and second communicating tubes.

It is preferable that a surface of the flow pass has been subjected to hydrophilic processing.

Thus, a liquid can be made to flow in a very small flow pass.

It is preferable that each of the first and second resistors has a comb shape.

Thus, even in a narrow region, each of the first and second resistors can have a great length, so that a large resistance value can be obtained.

It is preferable that the measurement device of the present invention further includes a third communicating tube connected to other part of the well than the parts of the well to which the first and second communicating tubes are connected and extending in a fourth direction different from the second and third directions; a third resistance bath connected to the third communicating tube; and a third resistor arranged in the third communicating tube or the third resistance bath.

Thus, the position of the biological sample contained in the electrolyte solution can be freely controlled. Furthermore, the degree of freedom of position control of the biological sample contained in the electrolyte solution is increased, so that the microelectrode can be freely formed in the well. That is, the degree of freedom of design of the inside of the well is improved.

It is preferable that the first and second communicating tubes are arranged so that a line extending along each said tubes extends toward said at least a microelectrode and has an opening toward said at least a microelectrode, and the third communicating tube is arranged so that the end portion of said at least a microelectrode is located substantially on a straight line extending along the third communicating tube.

Thus, in the well, the local flow of the electrolyte solution can be generated so as to flow toward any direction of front, back, right and left with respect to the microelectrode.

The measurement device may further include: another flow pass extending in the first direction; another pair of introduction orifices connected to both ends of said another flow pass, respectively; another concave well formed in said another flow pass; another reference electrode formed in said another flow pass; at least another microelectrode formed in said another well; another first communicating tube connected to said another well and extending in the second direction different from the first direction; another second communicating tube connected to other part of said another well than part of said another well to which said another first communicating tube is connected; another first resistance bath and another second resistance bath connected to said another communicating tube and said another communicating tube, respectively; and another first resistor and another second resistor arranged in said another first communicating tube and said another second communicating tube, respectively, or in said another first resistance bath and said another second resistance bath, respectively.

Thus, multiple measurements can be performed at the same time.

A measurement method according to the present invention is a method for measuring an electrical signal from a biological sample, the method comprising the steps of: a) preparing a measurement device including a flow pass extending in a first direction, a pair of introduction orifices connected to both ends of the flow pass, respectively, a concave well formed in the flow pass, a reference electrode formed in the flow pass, at least a microelectrode formed in the well, a first communicating tube connected to the well and extending in a second direction different from the first direction, a second communicating tube connected to other part of the well than part of the well to which the first communicating tube is connected and extending in a third direction different from the first and second directions, first and second resistance baths connected to the first and second communicating tubes, respectively, and first and second resistors arranged in the first and second communicating tubes, respectively, or the first and second resistance baths, respectively; b) introducing an electrolyte solution into the flow pass by reduction of a pressure in the flow pass to fill the flow pass; c) returning the pressure in the flow pass to an atmosphere pressure; d) arranging the biological sample in the well; e) closing up the flow pass; f) applying a current to the first or second resistor to bring said at least a microelectrode in contact with the biological sample; and g) measuring change in an electrical signal from the biological sample.

According to the measurement method of the present invention, when electrophysiological measurement of a biological sample led by an electrode, a highly accurate position controller and skilled operation, which have been conventionally needed, are no longer necessary. That is, electrophysiological measurement of a biological sample can be performed in a simple, accurate, high-speed and automatic manner.

The measurement method of the present invention may further include after the step f), the step h) of applying an electrical pulse to said at least a microelectrode.

Thus, an electrical reaction of a biological sample due to electric stimulation can be measured with high sensitivity.

The measurement method may further include the step i) of administering a drug from one of the pair of introduction orifices.

Thus, an electrical reaction of a biological sample to a drug can be measured in a simple manner.

BEST MODE FOR CARRYING OUT THE INVENTION

Hereinafter, embodiments of the present invention will be described with reference to the accompanying drawings.

Embodiment 1

Figure 1:
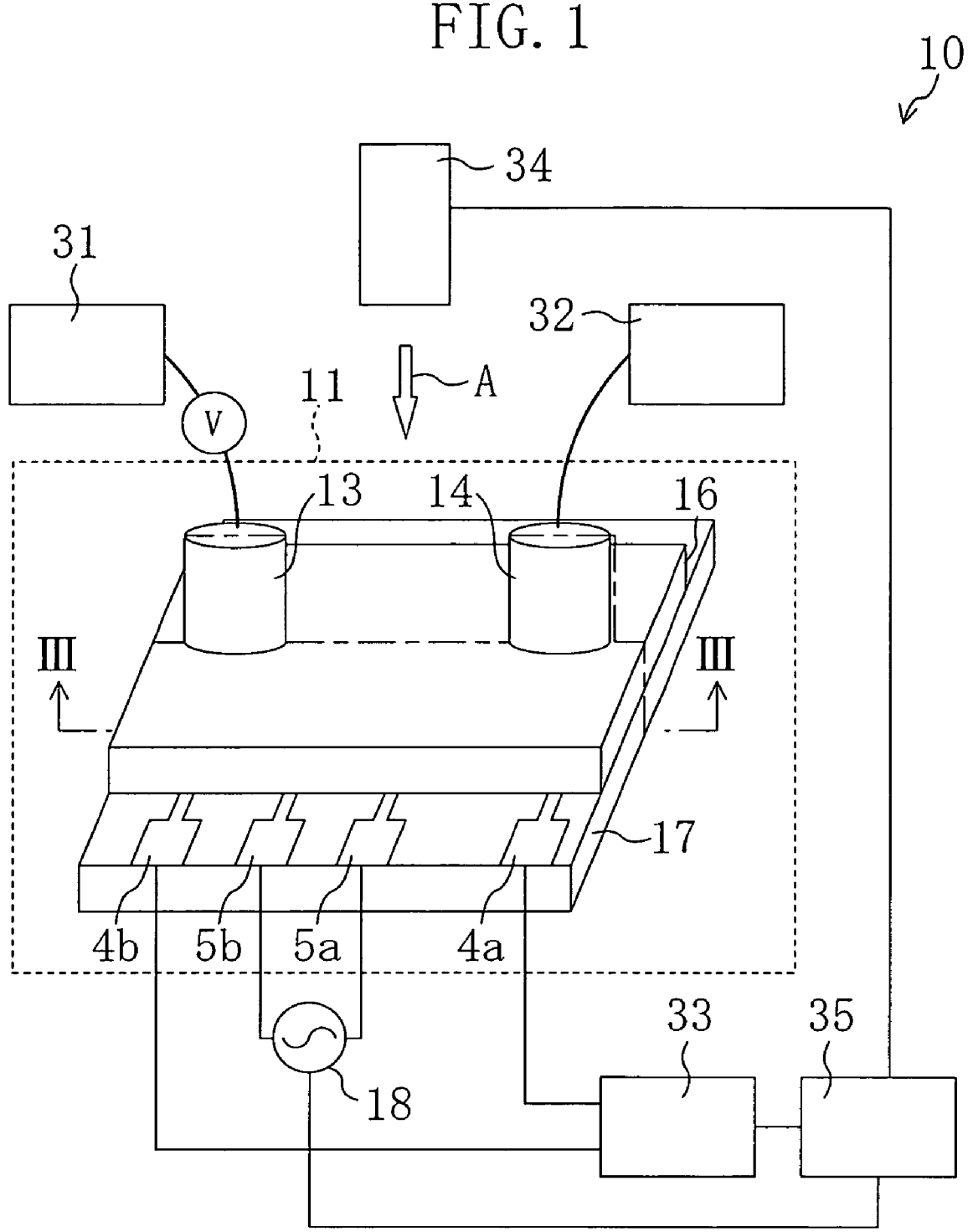
FIG. 1 is a diagram illustrating the structure of a measurement device according to EMBODIMENT 1 of the invention.
Figure 2:
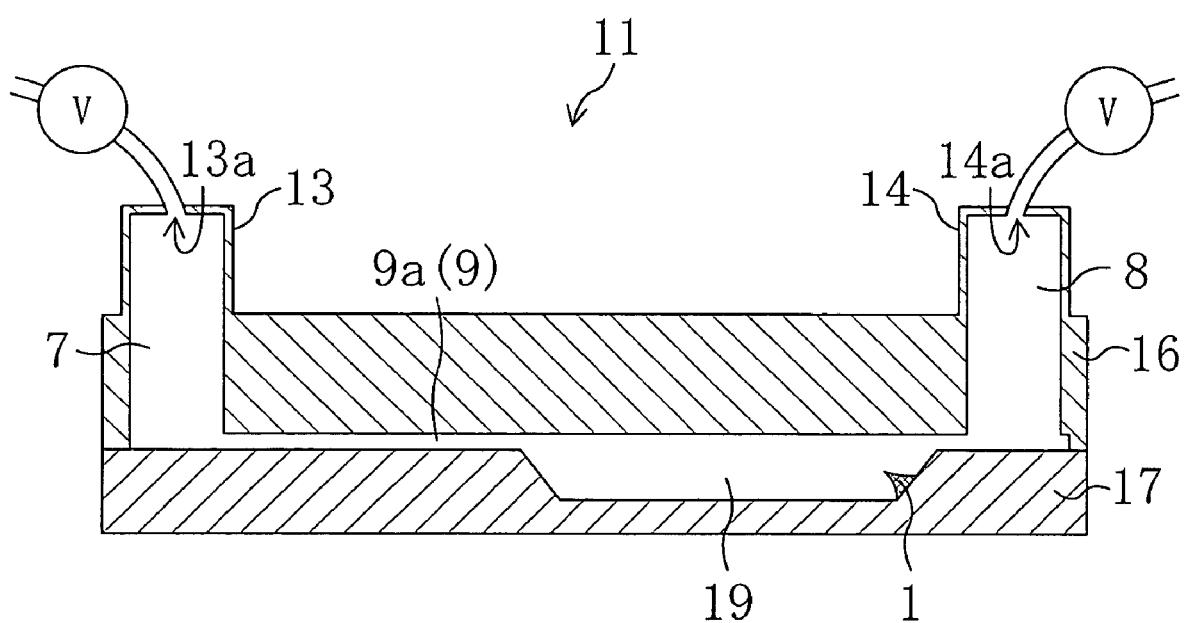
FIG. 2 is a cross-sectional view taken along the line III-III of FIG. 1.

FIG. 1 is a diagram illustrating the structure of a measurement device according to this embodiment. FIG. 2 is a cross-sectional view taken along the line III-III of FIG. 1.

As shown in FIG. 1, a measurement device 10 according to this embodiment includes a measurement cell 11, a current application section 18, pumps 31 and 32, a measuring section 33, an imaging section 34, and a calculator 35.

The measurement cell 11 includes a substrate 17, a substrate 16 provided on the substrate 17. The substrates 16 and 17 are bonded to each other. As shown in FIG. 1, terminals 4a, 4b, 5a and 5b are provided on the substrate 17.

The current application section 18 is, as shown in FIG. 1, electrically connected to the terminals 5a and 5b provided on the substrate 17.

The pumps 31 and 32 are, as shown in FIG. 1, connected to opening portions 13a and 14a formed in an inlet connector 13 and an outlet connector 14, respectively.

The measuring section 33 is connected to the terminals 4a and 4b, and the calculator 35 is electrically connected to the measuring section 33.

The imaging section 34 is arranged so as to be located directly on the measurement cell 11. As shown in FIG. 1, the imaging section 34 and the current application section 18 are electrically connected to the calculator 35 as necessary.

Next, the detailed structure of the measurement cell 11 will be described.

As shown in FIG. 1, the inlet connector 13 and the outlet connector 14 are provided on the substrate 16 constituting a measurement cell. In this embodiment, as shown in FIGS. 1 and 2, the inlet connector 13 and the outlet connector 14 are attached to the substrate 16 with an adhesive agent or the like. However, the present invention is not limited thereto, but the inlet connector 13 and the outlet connector 14 may be provided so as to make one unit together with the substrate 16. Moreover, as shown in FIG. 2, the insides of the inlet connector 13 and outlet connector 14 are cavities 7 and 8, which pass through the substrate 16. Furthermore, the opening portions 13a and 14a are provided in respective upper portions of the inlet connector 13 and the outlet connector 14, respectively. The cavities 7 and 8 of the insides of the inlet connector 13 and the outlet connector 14 are connected to the pumps 31 and 32, respectively, through tubes or the like. The cavities 7 and 8 of the insides of the inlet connector 13 and the outlet connector 14 are connected to the pumps 31 and 32, respectively, via a valve V.

Moreover, as shown in FIG. 2, a concave portion 9a is formed in the substrate 16. Thus, when the measurement cell 11 is formed by sticking the substrates 16 and 17 to each other, a flow pass 9 is formed in the measurement cell 11.

The substrate 17, as shown in FIG. 2, includes a concave well 19 and a protruding microelectrode 1 provided on a side wall surface of the well 19.

Figure 3:
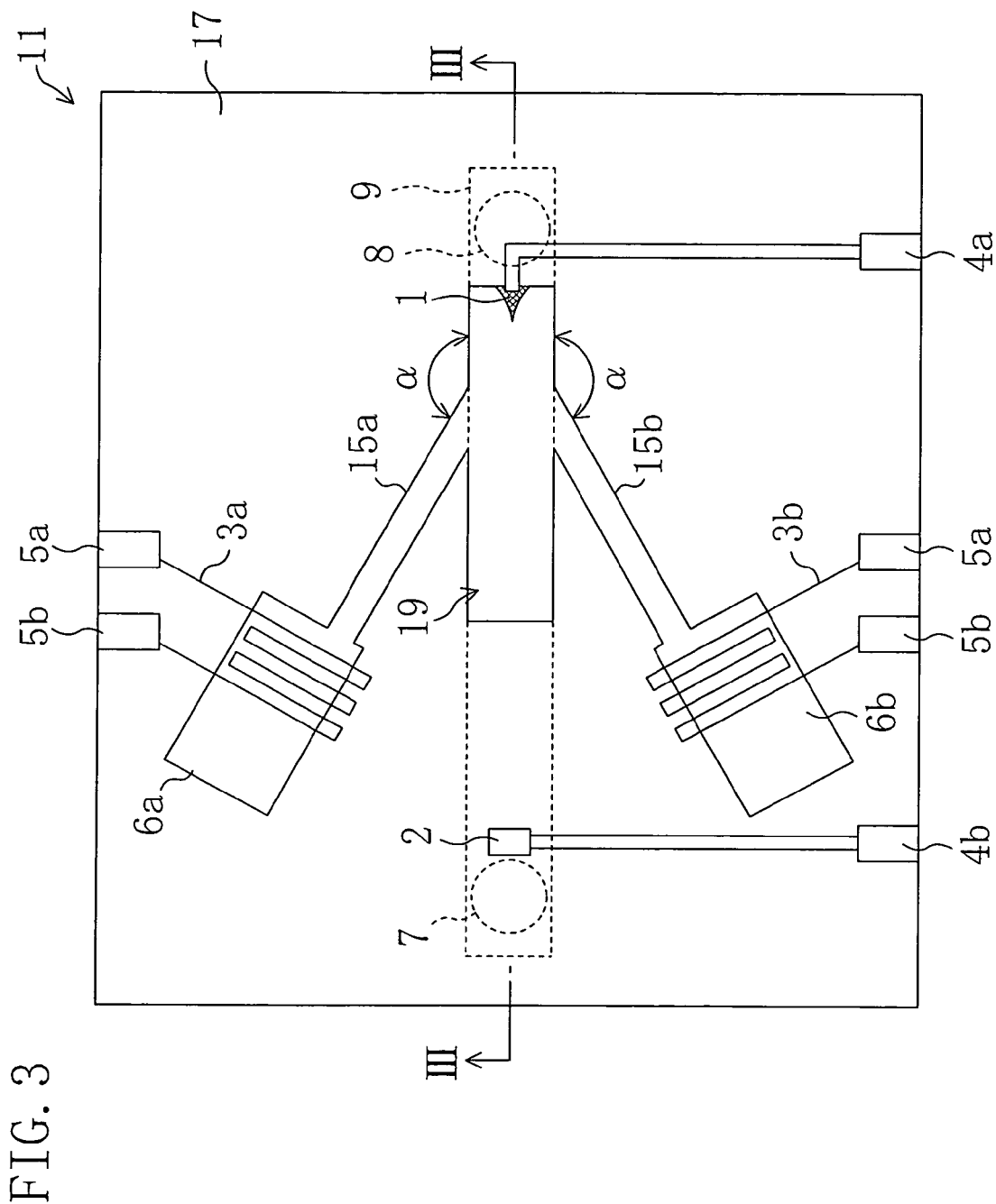
FIG. 3 is a perspective view of the measurement cell seen from the arrow A of FIG. 1.

More details of the structure of the measurement cell 11 will be described with reference to the FIG. 3, in addition to the FIGS. 1 and 2. FIG. 3 is a perspective view of the measurement cell 11 seen from the arrow A of FIG. 1. Note that a cross-sectional view taken along the line III-III of FIG. 3 corresponds to the cross-sectional view taken along the line III-III of FIG. 1, i.e., the cross-sectional view of FIG. 2. Moreover, in FIG. 3, the substrate 16 of the measurement cell 11 is omitted.

As shown in FIGS. 2 and 3, the substrate 16 is attached to the substrate 17 so that the cavities 7 and 8 are located over both ends of the flow pass 9, respectively.

As shown in FIG. 3, on the substrate 17 of the measurement cell 11, provided are the concave well 19, the protruding microelectrode 1 connected to the terminal 4a and provided on a side wall surface of the well 19, communicating tubes 15a and 15b connected to both side surfaces of the well 19 (i.e., the flow pass 9), respectively, so as to face to each other, resistance baths 6a and 6b connected to the communicating tubes 15a and 15b, respectively, thin resistors 3a and 3b arranged in the resistance baths 6a and 6b, respectively, and a reference electrode 2 connected to the terminal 4b.

The communicating tubes 15a and 15b are arranged so as to have line-symmetry with respect to the flow pass 9 (i.e., the well 19). Moreover, assume that an angle between the flow pass 9 (i.e., the well 19) and the communicating tube 15a or 15b is an angle α. The communicating tubes 15a and 15b are arranged so that the angle a is an obtuse angle at any time. That is, the communicating tubes 15a and 15b are arranged so that a straight line extending along the communicating tube 15a and a straight line extending along the communicating tube 15b intersect with each other toward the microelectrode 1.

Moreover, in this embodiment, in the same manner as the communicating tubes 15a and 15b, the resistance baths 6a and 6b are arranged so as to have line-symmetry with respect to the flow pass 9 (i.e., the well 19) and also the thin resistors 3a and 3b are arranged so as to have line-symmetry with respect to the flow pass 9.

Each of the communicating tubes 15a and 15b has a very small cross-sectional area, compared to the resistance baths 6a and 6b. The resistance baths 6a and 6b have an arbitrary shape.

The reference electrode 2 is arranged in the vicinity of the inlet 7 of the flow pass 9 formed in the substrate 16. Note that the reference electrode 2 may be located in any location in which the reference electrode 2 can be in contact with a liquid, and is preferably arranged in the flow pass 9 and the well 19. Accordingly, the reference electrode 2 can be formed on the substrate 17. However, when simpleness of fabrication is taken into consideration, the reference electrode 2 is preferably provided on the substrate 16.

As shown in FIGS. 1 and 3, the microelectrode 1 and the reference electrode 2 are connected to the measuring section 33 via the terminals 4a and 4b, respectively. As the measuring section 33, a current/voltage amplifier including a bridge-balancing circuit, a current stimulation circuit, and a capacity compensation mechanism and the like is preferably used in the micropipette electrode method.

As shown in FIGS. 1 and 3, the thin resistors 3a and 3b are connected to the current application section 18 via the terminals 5a and 5b, respectively. The current application section 18 applies a desired current to the thin resistors 3a and 3b.

As the substrate 17, a semiconductor substrate formed of a silicon substrate or the like is preferably used. If a semiconductor substrate is used as the substrate 17, the resistance baths 6a and 6b and the communicating tubes 15a and 15b can be formed by a semiconductor fabrication technique known by a person skilled in the art. Specifically, the resistance baths 6a and 6b and the communicating tubes 15a and 15b are preferably formed by wet etching. This is because when wet etching is used, by taking advantage of plane-directional selectivity, the substrate 17 (i.e., a measurement cell) having a highly accurate and fine structure can be obtained.

Note that either dry etching or wet etching is used, the above-described resistance baths and communicating tubes can be formed. When wet etching is performed, as an etchant, an isotropic etchant or an anisotropic etchant is selectively used according to need.

As the substrate 16, a transparent substrate is preferably used so that the flow pass 9 can be observed from the imaging section 34. The respective cavities 7 and 8 of the inlet and outlet connectors 13 and 14 provided on the substrate 16 and the flow pass 9 can be formed using a processing technique (specifically, cutting process, grinding process or the like) known by a person skilled in the art or a semiconductor fabrication technique known by a person skilled in the art. Specifically, as the substrate 16, a glass substrate is preferably used. Thus, the respective cavities 7 and 8 of the inlet and outlet connectors 13 and 14 provided on the substrate 16 and the concave portion 9a can be formed using a semiconductor fabrication technique known by a person skilled in the art with high accuracy.

The microelectrode 1 is formed of a conductive material. Specifically, in this embodiment, the microelectrode 1 is formed in a manner in which a single crystalline silicon is made into a shape having a micro-size protruding portion by under etching. A surface of the micro-size silicon protruding portion is coated with a metal thin film and then an edge portion of the protruding portion is removed. Thereafter, the micro-size silicon protruding portion is coated with an insulator. In this manner, the microelectrode 11 has a sharp protruding portion having a tip diameter of about 0.1 μm.

In this embodiment, the reference electrode 2, the terminals 4a, 4b, 5a and 5b, an interconnect for connecting the microelectrode 1 and the terminal 4a, an interconnect for connecting the reference electrode 2 and the terminal 4b, and the resistors 3a and 3b are formed using a thin film forming technique such as vacuum evaporation and sputtering. However, method for forming these members are not limited thereto, but these members may be formed by other methods known by a person skilled in the art.

Next, a solution introduction method of the measurement device 11 of this embodiment will be described with reference to FIG. 4.

Figure 4A:
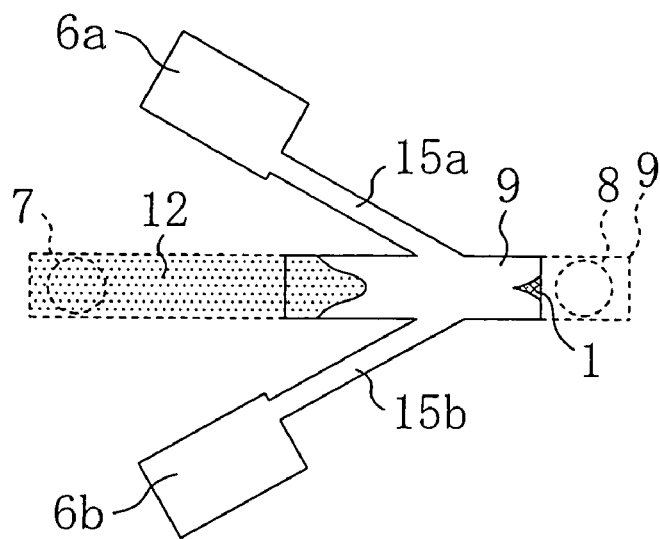
FIGS. 4(a), 4(b) and 4(c) are schematic diagrams illustrating the operation of a measurement device of EMBODIMENT 1.
Figure 4B:
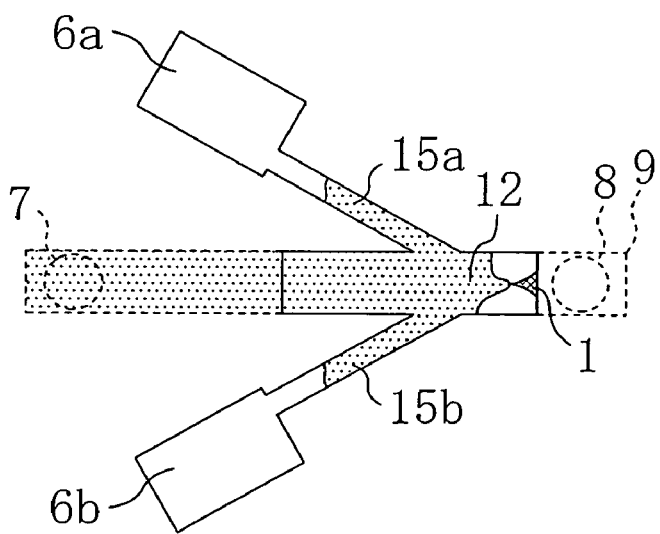
Figure 4C:
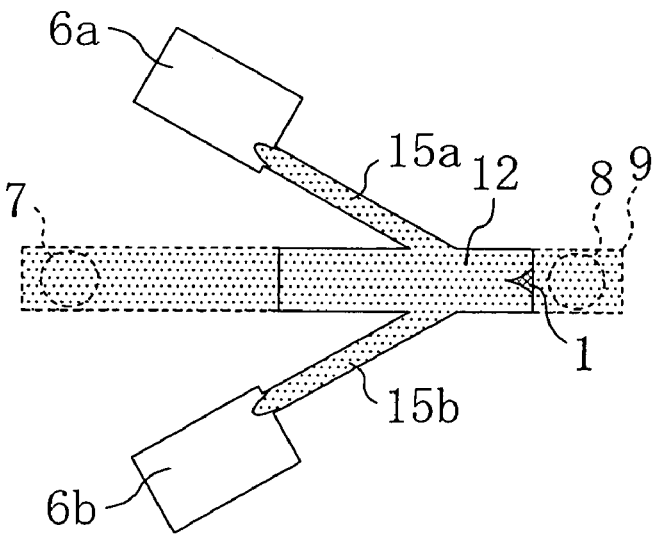

FIGS. 4(*a*), 4(*b*) and 4(*c*) are schematic diagrams illustrating a solution introduction method of a measurement device 11 of this embodiment.

First, a valve V connected to the connector having the inlet 8 of the flow pass 9 of the device is closed and then suction is performed by a pump 32 connected to the cavity 8 (i.e., the outlet connector 14) serving as an outlet of the flow pass 9. In this manner, a pressure in each of the flow pass 9, the communicating tubes 15a and 15b, and the resistance baths 6a and 6b is reduced to a pressure Pd slightly lower than an atmosphere pressure P1. Subsequently, as shown in FIG. 4(*a*), the valve V is opened to the air, so that an electrolyte solution 12 is injected into the flow pass 9 from the pump 31 connected to the valve V through the cavity 7 (i.e., the inlet connector 13).

At this time, a pressure in each of the resistance baths 6a and 6b connected to the flow pass 9 through the communicating tubes 15a and 15b, respectively, is the pressure Pd lower than the atmosphere pressure P1. Accordingly, as shown in FIG. 4(*b*), the electrolyte solution 12 injected into the flow pass 9 fills the well 19, as well as the communicating tubes 15a and 15b, to flow toward the cavity 8 (i.e., the outlet connector 14) serving as an outlet.

Subsequently, the electrolyte solution 12 reaches the cavity 8 as the outlet of the flow pass 9, the suction of the pump 32 connected to the outlet connector 14 is stopped. Then, the cavity 8 serving as the outlet is opened to the air by valve operation or the like to return the pressure in the flow pass 9 back to the atmosphere pressure P1. At this time, the pressures in the resistance baths 6a and 6b are still substantially at Pd. Thus, the electrolyte solution 12 filling the communicating tubes 6a and 6b flows towards the resistance baths 6a and 6b. When each of the pressures in the resistance baths 6a and 6b becomes equal to P1, the flow of the electrolyte solution 12 stops, as shown in FIG. 4(*c*). At this time, the injection of the electrolyte solution 12 is stopped and the valve V connected to the cavity 7 (i.e., the inlet connector 13) serving as an inlet is closed.

Next, a biological sample 21 (a cell in this embodiment) is introduced in the electrolyte solution 12. In this embodiment, when the biological sample 21 is introduced, properties obtained according to the shape of the slow pass 9 are used.

The flow pass 9 is a space whose height is very small, as shown in FIG. 2. There is a characteristic in which with a small space filled with a liquid like the flow pass 9, when another liquid further flows therein, the liquid introduced later tends to be a laminar flow. When a liquid flowing in the flow pass 9 flows as a laminar flow, the liquid flowing substantially does not mix with the liquid with which the well 19 is filled and passes in an upper stream. In this embodiment, a sample solution containing the biological sample 21 is injected through the cavity 7 (i.e., the inlet connector 13) from the pump 31 connected to the valve V into the flow pass 9 filled with the electrolyte solution 12. In this case, the biological sample 21 is monitored, and when the biological sample 21 reaches the upper portion of the well 19, the injection of the sample solution is stopped. Thus, the laminar flow disappears in the flow pass 9 and diffusion of the electrolyte solution 12 becomes superior, so that the biological sample 21 is introduced into the well 19.

Note that in this embodiment, the introduction of the biological sample 21 has been described. However, this embodiment is not limited thereto, but introduction and removal of an agent can be performed in the exactly same manner as described above.

Figure 5:
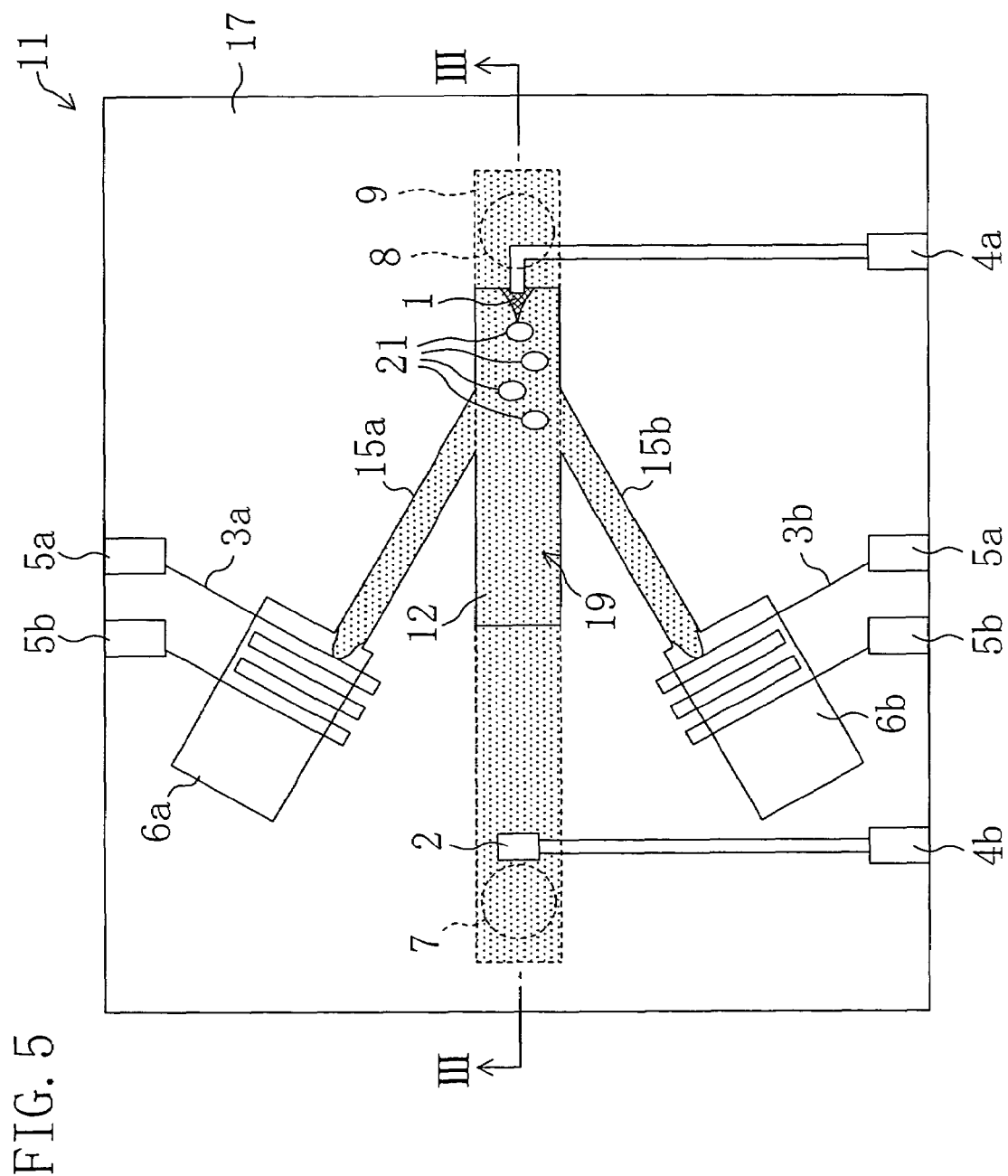
FIG. 5 is a perspective view of the measurement cell seen from the arrow A of FIG. 1.

Finally, as shown in FIG. 5, the flow pass 9, the well 19 and the communicating tubes 15a and 15b are filled with the electrolyte solution 12.

Note that in this embodiment, as the electrolyte solution 12, an extracellular fluid for measuring an intracellar potential of a cell, i.e., the biological sample 21, is used. As the extracellular fluid, a saline solution containing as a main component NaCl of 20 mM to 400 mM, various kinds of nutrients, growth factors, culture medium containing an antibiotic or the like can be used.

Specifically, the measurement device 10 is designed so that the volumes of the resistance baths 6a and 6b are much larger than those of the communicating tubes 15a and 15b, respectively, or the volume of the well 19. Therefore, by appropriately adjusting the pressure in the resistance baths 6a and 6b, a vapor-liquid interface can be controlled to be located at a desired position in the communicating tubes 15a and 15b in a simple manner. More specifically, the volumes of the resistance baths 6a and 6b are preferably five times as large as or more than those of the communicating tubes 15a and 15b.

Figure 6A:
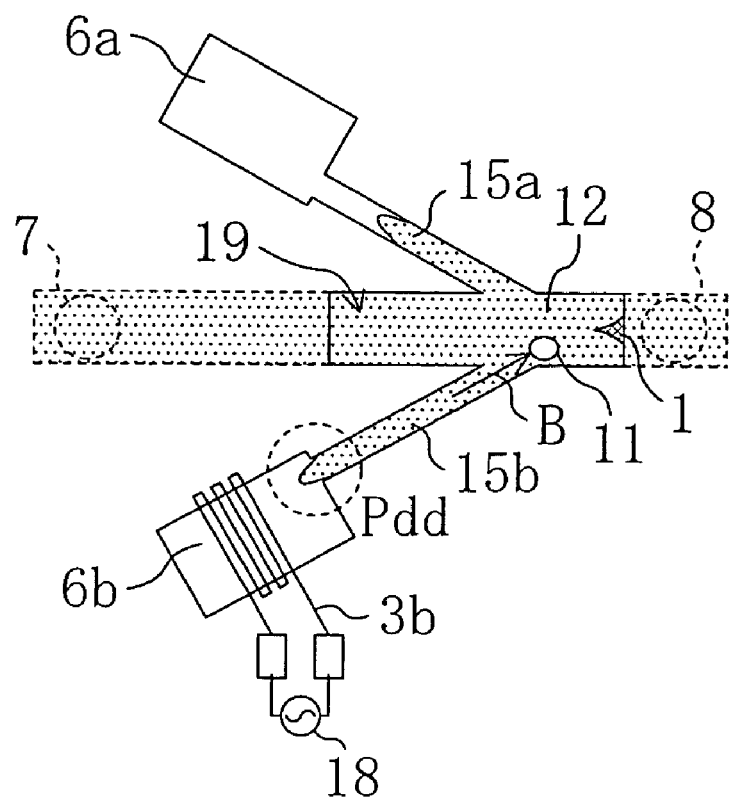
FIGS. 6(a) and 6(b) are schematic diagrams illustrating the outline of the principle on which the introduction of a cell into an electrode is based.
Figure 6B:
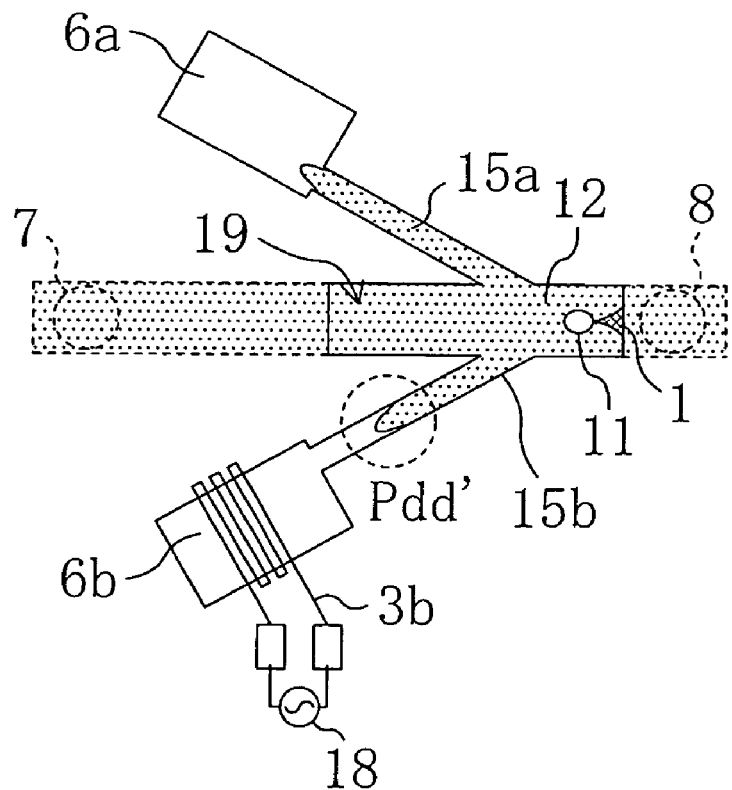

Next, the outline of the principle on which the introduction of a cell into an electrode performed in the measurement device 10 of this embodiment is based will be described with reference to FIG. 6. FIGS. 6(a) and 6(b) are schematic diagrams illustrating the outline of the principle on which the introduction of a cell into an electrode is based. Here, a case in which a current is applied to the thin film resistor 3b arranged in the resistance bath 6b of the measurement device 10 will be described as an example.

First, when a current is applied to the thin film resistor 3b by the current application section 18, an electrical energy W represented by Equation 1 is consumed in the thin film resistor 3b.

$$W = RI^2 \quad \text{[Equation 1]}$$

where R is a resistance value [$\Omega \cdot m$] of the thin film resistor 3b and I is a current [A] flowing in the thin film resistor 3b.

The consumed electrical energy W is transformed into heat energy. This heat energy expands air in the resistance base 6b. Accordingly, as shown in FIG. 6(a), a pressure in the resistance bath 6b is made to be Pdd, and at the same time, the interfacial tension of the vapor-liquid interface of the communicating tube 15b connected to the resistance bath 6b is reduced. Since the interfacial tension of the vapor-liquid interface in the cavity 8 serving as the outlet of the flow pass 9 is not changed, an equilibrium in the interfacial tension of the vapor-liquid interface between the communicating tube 15b and the communicating tube 15a is lost. Accordingly, the electrolyte solution 12 flows from the resistance bath 6b to the well 19 in the direction which the arrow B of FIG. 6(a) points (i.e., toward the resistance bath having a lower temperature). The biological sample 21 moves according to the flow of the electrolyte solution 12 is led by the microelectrode 1 to be inserted.

Next, when current supply to the resistor 6b is stopped, part of the heated air in the resistance bath 6b is returned to an ambient temperature and the pressure in the resistance bath 6b becomes Pdd'. An equilibrium between the interfacial tensions is achieved again, so that the biological sample 21 is held as shown in FIG. 6(b) at a location to which the biological sample 21 has moved. The volume of the communicating tube 15b is very small and the electrolyte solution 12 has a small heat capacitance. Therefore, the electrolyte solution 12 moves very quickly.

In this embodiment, when the activity of a cell is measured, the cavity 7 and the cavity 8 which serve as an inlet and an outlet, respectively, are closed. Thus, a distance x ($\mu m$) by which the electrolyte solution 12 has been moved through the communication tube 15b is in proportion to a difference between the interfacial tension of the vapor-liquid interface in the communicating tube 15a and the interfacial tension of the vapor-liquid interface in the communicating tube 15b. Therefore, by controlling a current value Ib and a current variation speed $\Delta Ib$ (A/s) of a current applied to the thin film resistor 3b or by controlling a difference between current values Ia and Ib of currents applied to the thin film resistors 3a and 3b, respectively, and a difference between current variation speeds $\Delta Ia$ and $\Delta Ib$, a difference between the interfacial tensions is adjusted. Thus, the distance x ($\mu m$) of a movement of the vapor-liquid interface in the communicating tube 15a and a moving speed $\Delta x$ ($\mu m/s$) for the vapor-liquid interface in the communicating tube 15a are adjusted.

In this embodiment, the case in which the vapor-liquid interface in the communicating tube 15b is moved has been described. However, when the vapor-liquid interface in the communicating tube 15a is moved, the exactly same operation is performed.

In this embodiment, while the biological sample 21 is being monitored, the location of the biological sample 21 is feedback-controlled. An image of the biological sample 21 is digitized by the imaging section 34 (e.g., CCD) through the transparent substrate 16, the digitized image is input into the calculator 35, and then the amount of a current to be made to flow in each of the thin film resistors 3a and 3b is calculated based on image information such as the amount of a movement of the biological sample 21. The measurement device 10 may further include means for automatically applying a current of a current value obtained by the calculation to the current application section 18. Needless to say, the above-described operation may be performed in a manual manner by a technician. However, by automating the above-described operation, measurement can be preformed in a more simple manner.

As has been described, in the measurement device 10 of this embodiment, the current values Ia and Ib applied to the thin film resistors 3a and 3b, respectively, and the current variation speeds $\Delta Ia$ and $\Delta Ib$ (A/s) are controlled to adjust the difference between the interfacial tensions of the vapor-liquid interfaces in the resistance baths 6a and 6b (or the communicating tubes 15a and 15b), so that the distance and speed of a movement of the vapor-liquid interface in each of the communicating tubes 15a and 15b is adjusted.

Thus, in the measurement device 10 of this embodiment, a local flow of the electrolyte solution 12 can be generated in the well 19, the biological sample 21 is accurately and quickly led to the microelectrode 1 by using the local flow, and then an electrophysiological measurement of the biological sample 21 can be performed. Therefore, a highly accurate position controller and skilled operation, which have been needed in the known device of this type, are no longer necessary.

Moreover, with the measurement device 10 of this embodiment, a chemical substance such as a nerve stimulator and a chemical synapse messenger can be administered to a cell 21 in the well 19, so that a highly accurate measurement as an intracellular recording method in which ion channel properties and chemical synapse of a cell are measured can be performed in a simple manner.

Specifically, in the measurement device 10, the communicating tubes 15a and 15b are arranged so as to substantially have line-symmetry with respect to the flow pass 9 (i.e., the well 19). Thus, a local flow of the electrolyte solution 12 generated in the well 19 can be generated between the communicating tubes 15a and 15b in bilateral directions (i.e., in the right and left directions when viewed from the microelectrode 1).

Furthermore, as shown in FIG. 3, assume that an angle between the flow pass 9 (i.e., the well 19) and each of the communicating tubes 15a and 15b is an angle a. The communicating tubes 15a and 15b are arranged so that the angle a is an obtuse angle at any time. Thus, a local flow of the electrolyte solution 12 in the well 19 can be generated toward the microelectrode 1 at any time.

As can be understood from the description above, in the measurement device 10 of this embodiment, a local flow of the electrolyte solution 12 can be two-dimensionally generated in a horizontal plane.

Moreover, in this embodiment, the communicating tubes 15a and 15b are arranged so as to substantially have line-symmetry with respect to the flow pass 9 (i.e., the well 19). Thus, calculation of a difference between the interfacial tensions of the vapor-liquid interfaces in the communicating tubes 15a and 15b can be simplified very much.

Furthermore, in this embodiment, the resistance baths 6a and 6b are arranged so as to have line-symmetry with respect to the flow pass 9 (i.e., the well 19) in the same manner as the communicating tubes 15a and 15b. Thus, calculation of a difference between the interfacial tensions of the vapor-liquid interfaces between the resistance baths 6a and 6b(or the communicating tubes 15a and 15b) can be further simplified. Therefore, the difference between the interfacial tensions of the vapor-liquid interface can be simplified in a very simple manner.

Furthermore, in the measurement device 10 of this embodiment, the reference electrode 2 is arranged in the vicinity of the inlet 7 of the flow pass 9 formed on the substrate 16. However, the reference electrode 2 may be located in any place as long as the reference electrode 2 is in contact with the electrolyte solution 12 when the flow pass 9 is filled with the electrolyte solution 12. Specifically, to perform an accurate measurement, the reference electrode 2 is preferably provided in the outside of the well 19 in which a local flow of the electrolyte solution 12 is generated.

Next, application examples for using the measurement device 10 of this embodiment will be described.

(Application Example 1: Measurement of the Action Potential of a Cell Stimulated by a Current)

The measurement device 10 of this embodiment can measure an electric signal from a cell by a voltage clamp method and a current clamp method in the same manner as the intracellular recording method using the known glass micropipette.

Specifically, as described above, the cell 21 is led to the microelectrode 1, the microelectrode 1 is inserted into the cell 21, and then the potential of the microelectrode 1 with respect to the reference electrode 2 is measured in the measuring section 33.

Moreover, a current pulse generator is provided in the measuring section 33 and the microelectrode 1 is connected to the current pulse generator. Then, a current stimulation is given from the microelectrode 1 and the cell 21 via the terminal 4a. Thus, the depolarization of the cell due to the current stimulation, a temporary action potential of the cell and the like can be calculated by the calculator 35.

(Application Example 2: Measurement of the Membrane Potential of a Cell Stimulated by Drug Administration)

The measurement device 10 of this embodiment can be used for measuring ion channel properties of a cell. Measurement of channel properties of a cell is performed by administering a chemical substance such as a nerve stimulator and a chemical synapse messenger to the cell 21 by the inlet connector 13 (cavity 7), the outlet connector 14 (cavity 8) and pumps 31 and 32 connected to the inlet connector 13 and the outlet connector 14, respectively.

In another way, a drug can be also injected by an inkjet method using a voltage device, a method using a fine pressure pump or a microfluid drive unit, a method disclosed in Japanese Laid-Open Patent Publication No. 10-337177, an electroporation method or the like.

For example, electroporation is a technique in which a DC pulse is applied between a drug reservoir and a target to which a drug is to be injected, thereby injecting a desired amount of the drug. Specifically, after the flow pass 9 has been filled with the electrolyte solution 12 and the cell 21 and a drug has been added to the electrolyte solution 12 in the well 19, a DC pulse is applied between the reference electrode 2 and the microelectrode 1 to inject a desired amount of the drug into the cell 21.

In this embodiment, the microelectrode 1 is provided on a wall surface of the well 19, but may be provided on a bottom surface of the well 19.

Moreover, in this embodiment, the microelectrode 1 may be provided plural in number per the reference electrode 2 in the well 19. When the microelectrode 1 is provided plural in number, the plurality of microelectrodes 1 may be connected to the terminal 4a or may be connected to a plurality of terminals, respectively. However, when the microelectrode 1 is provided plural in number, the surface area of the reference electrode 2 is preferably larger than that of the total area of the plurality of microelectrodes 1. This is for improving measurement stability against disturbances such as a solution flow.

When the microelectrode 1 is provided plural in number in the well 19, with a cell 21 fixed to each of the microelectrodes 1, all of cells can be measured at a time or each cell can be measured separately. More specifically, a cell as a biological sample is not necessarily alive. Then, assume that, for example, the survival rate of cells is 90%. In the measurement device 10 of this embodiment having the structure in which the microelectrode 1 is provided plural in number in the well 19, stochastically, data for substantially nine cells can be obtained by one measurement. This shows that this embodiment also has the effect of improving measurement efficiency.

In this embodiment, the connectors 13 and 14 are attached to the substrate 16 by an adhesive agent or the like. However, the present invention is not limited thereto, but the connectors 13 and 14 may be formed as one unit together with the substrate 16.

Materials used as the substrate 16 and the substrate 17 includes: semiconductor materials represented by a single crystalline silicon, amorphous silicon, silicon carbide, silicon oxide and silicon nitride; composite materials of these semiconductor materials represented by SOI (silicon on insulator); inorganic materials represented by glass, quartz glass, alumina, sapphire, ceramics, forsterite and photosensitive glass; organic materials represented by polyethylene, ethylene, polypropylene, polyisobutylene, polyethylene terephthalate, unsaturated polyester, fluorine-containing-resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenolic plastic, urea resin, epoxy resin, melamine resin, styrene acrylonitrile copolymer, acrylonitrile butadiene-styrene copolymer, polyphenylene oxide, and polysulfone; a novolac resin-diazonaphthoquinone (DNQ) type photosensitive material containing novolac resin as base resin; polymetyl metacrylate (PMMA); a copolymer containing PMMA; polyethylene sulfone; polyhexafluorobutyl methacrylate; polymethyl isopropenyl ketone (PMIPK); polydimethyl siloxane (PDMS); and photosensitive materials containing an azide compound including cyclopolyisoprene as a base polymer (e.g., 2-6-di-4-methyl cychlo hexanon). However, materials used as the substrate 16 and the substrate 17 are not limited thereto. Among these, amorphous silicon, single crystalline silicon, or glass is preferably used as the substrates 16 and 17.

Note that the concave portion 9a located in the substrate 16 and constituting the flow pass 9 and the surface of the wall 19 located in the substrate 17 are preferably subjected to hydrophilic treatment. Thus, a fluid can flow into a very small flow pass 9.

Each of the microelectrode 1 and the reference electrode 2 is formed of an electrode material, such as precious metal materials including platinum, platinum black, gold, palladium, rhodium, silver, mercury, tungsten, and compounds of these metals, or a carbon material represented by graphite, glassy carbon, pyrolytic graphite, carbon paste, and carbon fiber. However, materials for the microelectrode 1 and the reference electrode 2 are not limited thereto. Note that the microelectrode 1 and the reference electrode 2 may be coated by a conductive high polymer. Thus, a stable fixed electrode can be formed. Moreover, the electrodes can be coated by a monomolecular film.

The thin film resistors 3a and 3b can be formed of a material such as precious metals including platinum, platinum black, gold, palladium, rhodium, silver, mercury, tungsten, nickel, titanium and compounds of these metal, a carbon material represented by graphite, glassy carbon, pyrolytic graphite, carbon paste, and carbon fiber, and other materials such as Si, Ge, ZnO, CdS, $TiO_2$, GaAs, and titanium. However, materials for the thin film resistors 3a and 3b are not limited thereto. Note that as the microelectrode 1 and the reference electrode 2, the thin film resistors 3a and 3b may be coated by conductive macromolecules. Thus, a stable thin film resistor can be formed. Moreover, the resistors can be coated by a monomolecular film.

In this embodiment, the resistance baths 6a and 6b are filled with air. However, fillers to fill the resistance baths 6a and 6b are not limited to air, but any gases and liquids which can change an interfacial tension with the electrolyte solution 12 may be used.

Note that in this embodiment, the thin film resistors 3a and 3b are arranged in the resistance baths 6a and 6b, respectively. However, if the thin film resistors 3a and 3b are arranged in the communicating tubes 15a and 15b, the measurement device 10 of this embodiment can be operated in much the same manner. Moreover, each of the thin film resistors 3a and 3b preferably has a comb shape. Thus, even in a narrow region, each of the first and second resistors can have a great length, so that a large resistance value can be obtained.

Moreover, in this embodiment, the pumps 31 and 32 are used. However, the present invention is not limited thereto, but syringes may be used instead of the pump 31 and 32.

Embodiment 2

In this embodiment, a measurement cell 11' which can be used instead of the measurement cell 11 in the measurement device 10 of EMBODIMENT 1 will be described with reference to the accompanying drawings. Note that each member also shown in EMBODIMENT 1 is identified by the same reference numeral for the purpose of simplicity.

The measurement cell 11' of this embodiment has substantially the same appearance as that of the measurement cell 11 of EMBODIMENT 1. Thus, in this embodiment, a case where the measurement cell 11 is replaced by the measurement cell 11' will be described.

Figure 7:
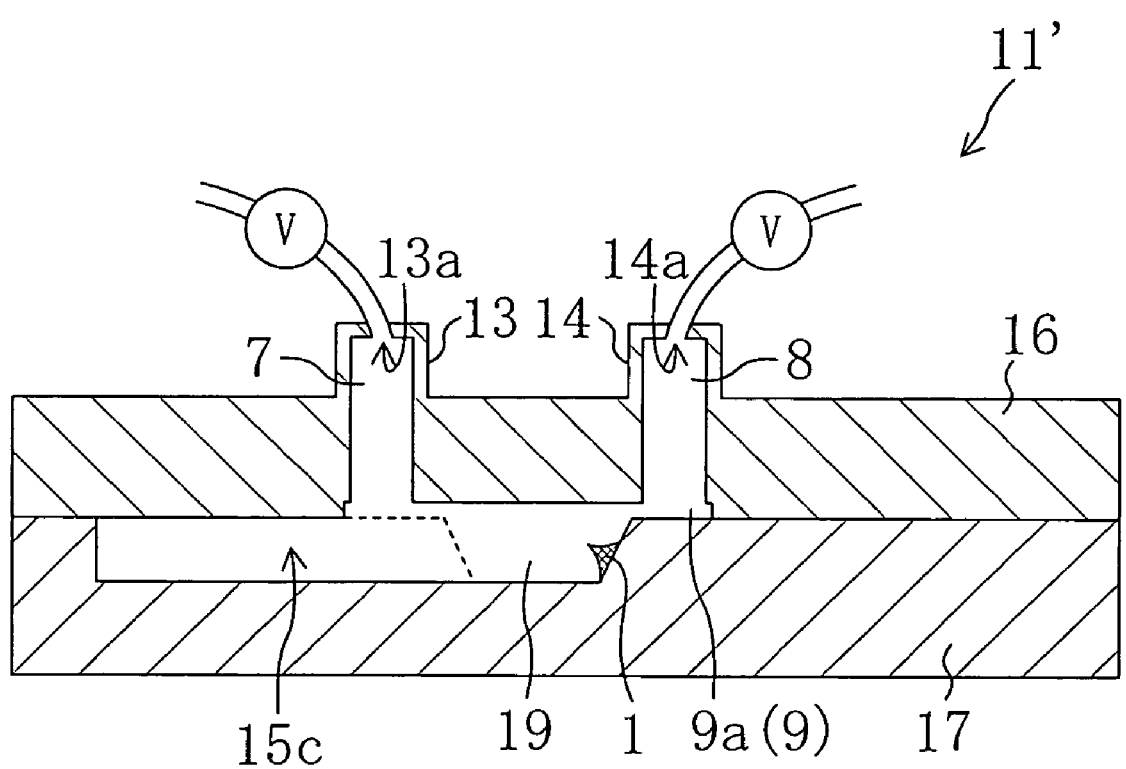
FIG. 7 is a diagram illustrating the structure of a measurement device according to EMBODIMENT 2 of the invention.
Figure 8:
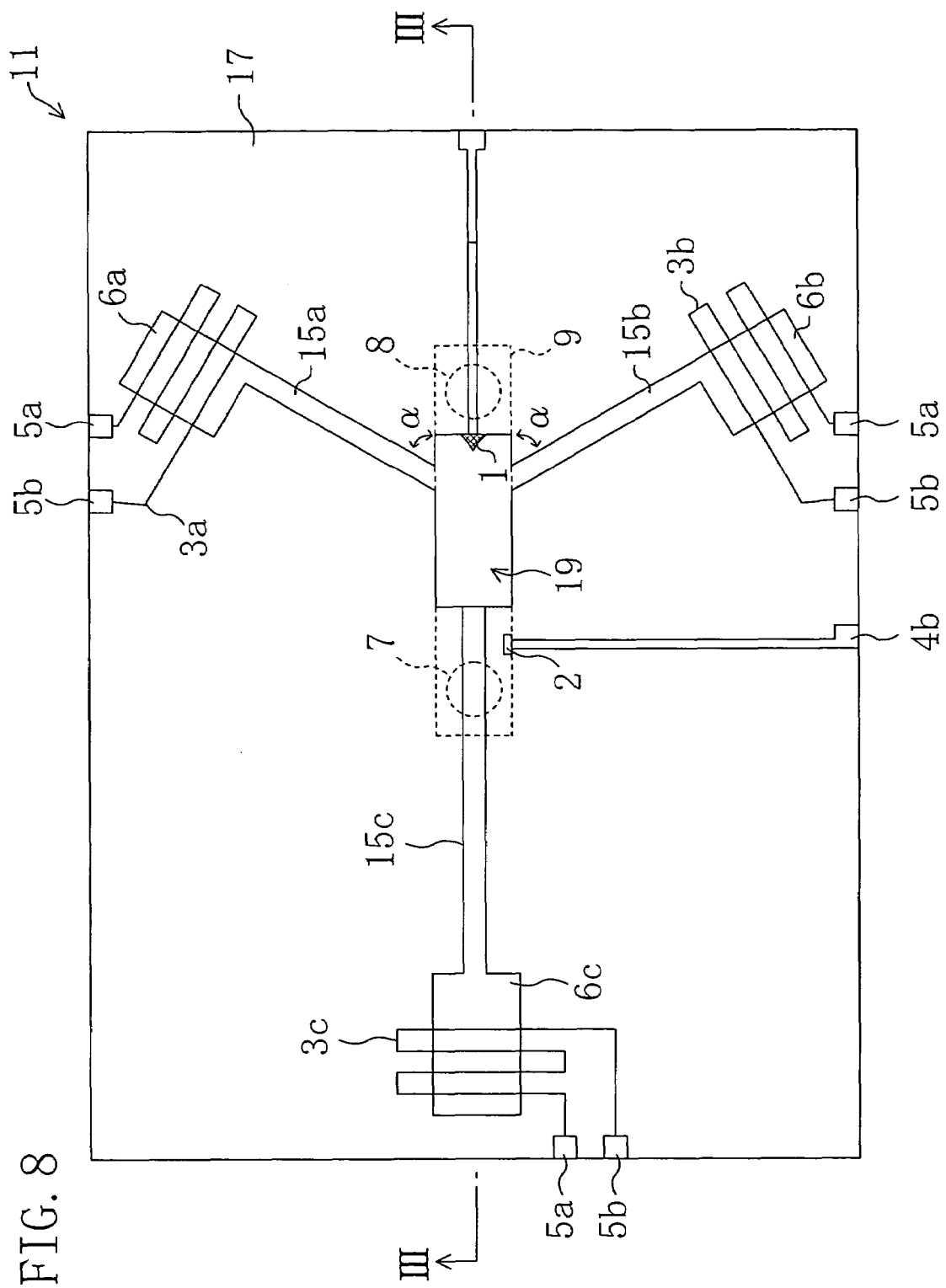
FIG. 8 is a cross-sectional view taken along the line III-III of FIG. 1.

FIG. 7 is a cross-sectional view taken along the line III-III of FIG. 1. FIG. 8 is a perspective view of the measurement cell 11' seen from the arrow A of FIG. 1. Note that a cross-sectional view taken along the line III-III of FIG. 8 corresponds to the cross-sectional view of FIG. 7. Moreover, in FIG. 8, the substrate 16 of the measurement cell 11' is omitted.

The measurement cell 11' has substantially the same structure as that of the measurement cell 11 of EMBODIMENT 1. However, as shown in FIGS. 7 and 8, the measurement cell 11' is different from the measurement cell 11 in that a communicating tube 15c connected to the well 19 (i.e., the flow pass 9), a resistance bath 6c connected to the tube 15c, and a thin film resistor 3c arranged in the resistance bath 6c are provided.

Thus, in the measurement cell 11', a local flow of the electrolyte solution 12 can be generated so as to flow toward any direction of front, back, right and left in a horizontal plane in the well 19 (i.e., totally freely in a two dimensional manner). Therefore, with the measurement cell 11' of this embodiment, the position of the biological sample 21 contained in the electrolyte solution 12 can be controlled more freely than in the case where the measurement cell 11 of EMBODIMENT 1 is used.

Furthermore, the degree of freedom of position control of the biological sample 21 contained in the electrolyte solution 12 is increased, so that the microelectrode 1 can be freely formed in the well 19. That is, the degree of freedom of design for the inside of the well 19 is improved.

In the measurement cell 11 of this embodiment, the communicating tube 15c connected to the well 19 (i.e., the flow pass 9) so as to face the microelectrode 1, the resistance bath 6c connected to the communicating tube 15c, and the thin film resistor 3c arranged in the resistance bath 6c are provided. Thus, a local flow of the electrolyte solution 12 in the well 19 can be generated in the direction toward the microelectrode 1.

Moreover, as shown in FIG. 8, assume that an angle between the flow pass 9 (i.e., the well 19) and each of the communicating tubes 15a and 15b is an angle a. The communicating tubes 15a and 15b are arranged so that the angle a is an acute angle at any time. That is, the communicating tubes 15a and 15b are arranged so that a line extending along each of the tubes 15a and 15b extends toward the microelectrode 1 and each of the tubes 15a and 15b has an opening, toward the microelectrode 1. Thus, a local flow of the electrolyte solution 12 in the well 19 can be generated to move away from the microelectrode 1 at ay time.

Furthermore, the communicating tubes 15a and 15b are arranged so as to have line-symmetry with respect to the flow pass 9 (i.e., the well 19). Thus, a local flow of the electrolyte solution 12 in the well 19 can be generated in bilateral directions between the communicating tubes 15a and 15b (i.e., in the right and left directions viewed from the microelectrode 1).

As can be seen from the description above, the measurement cell 11' of this embodiment has a structure having a high symmetry as shown in FIG. 8. Thus, calculation of differences among the interfacial tensions of the vapor-liquid interfaces in the resistance baths 6a, 6b and 6c (or the communicating tubes 15a, 15b and 15c) can be simplified. Therefore, the differences among the interfacial tensions can be adjusted in a simple manner.

More specifically, it is preferable that in the measurement cell 11' of this embodiment, the angle between the flow pass 9 (i.e., the well 19) and each of the communicating tubes 15a and 15b is about 60degrees and the communicating tube 15c is provided so as to face the microelectrode 1. Thus, calculation of differences among the interfacial tensions of the vapor-liquid interfaces in the resistance baths 6a, 6b and 6c (or the communicating tubes 15a, 15b and 15c) can be simplified most. Therefore, the differences among the interfacial tensions can be adjusted in a very simple manner.

Note that in this embodiment, a structure in which the communicating tubes extending in three different directions, the resistance baths connected to the communicating tubes, respectively, and the resistors connected to the communicating tubes, respectively, are provided is used. However, an additional communicating tube extending in a different direction from any one of the three directions, an additional resistance bath connected to the communicating tube, and an additional resistor connected to the communicating tube may be further provided. Thus, the biological sample 21 may be led in the direction in which the additional communicating tube extends in a simple manner. That is, the biological sample 21 can be led in an increased number of directions in a simple manner. Therefore, the biological sample 21 can be led to the microelectrode 1 with higher accuracy.

Embodiment 3

Figure 9:
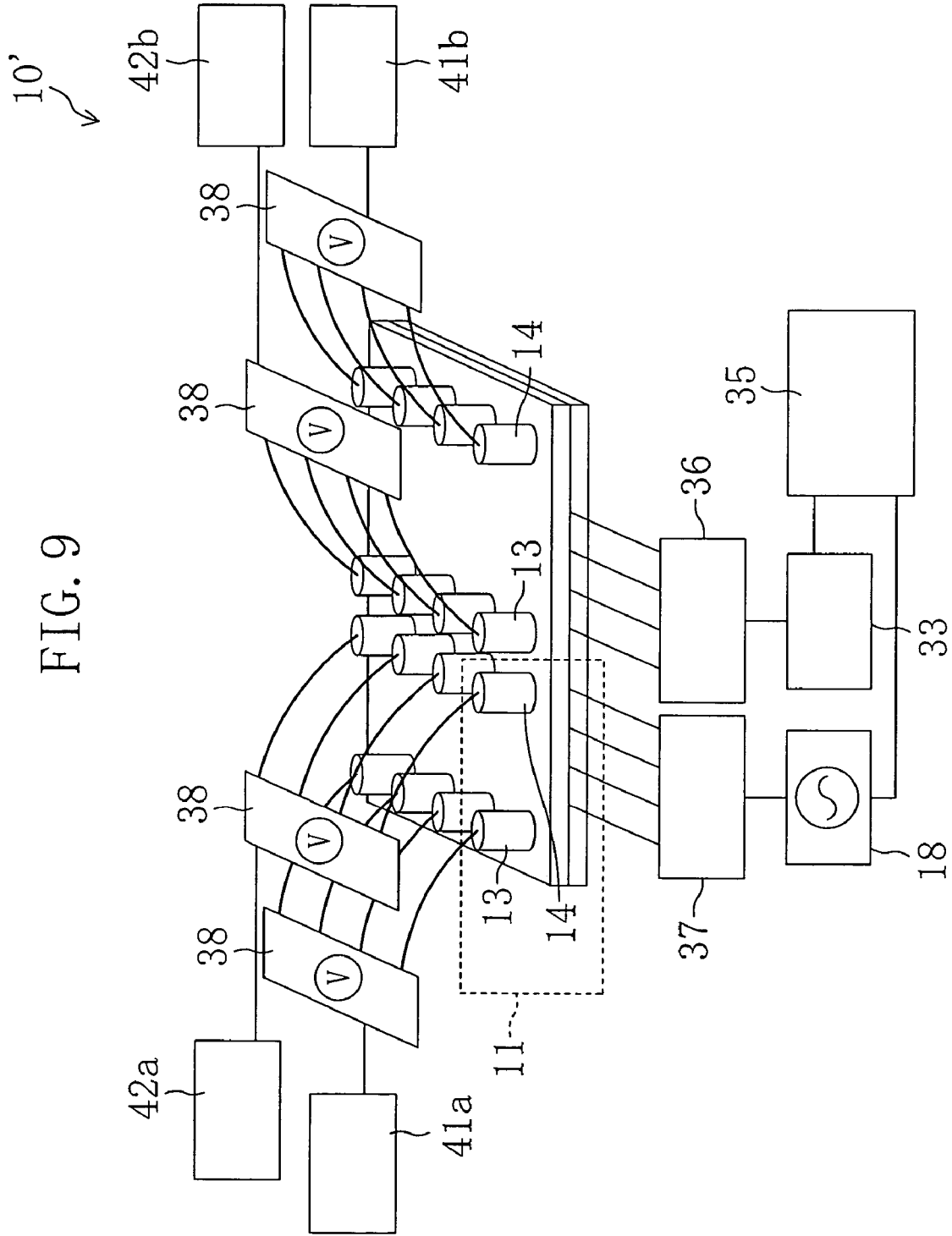
FIG. 9 is a perspective view of the measurement cell seen from the arrow A of FIG. 1.

FIG. 9 is a diagram illustrating the structure of a measurement device of this embodiment.

As shown in FIG. 9, the measurement device 10' of this embodiment includes the measurement cell 11 or the measurement cell 11', as the measurement device 10 of EMBODIMENT 1 or EMBODIMENT 2. More specifically, in the measurement device 10' of this embodiment, the measurement cell 11 or the measurement cell 11' is provided plural in number. The plurality of measurement cells 11 or 11' are integrated in a matrix pattern. The structure of the measurement cell 11 or 11' is exactly the same as that of EMBODIMENT 1 or EMBODIMENT 2.

Inlet connectors 13 and outlet connectors 14 provided in each of the plurality of measurement cells 11 or 11' are connected to flow pass switchers 38 each including a valve and a pump. A structure is used in which the inlet connectors 13 and the outlet connectors 14 are made to be interchangeably used as outlets and as inlets by the flow pass switcher 38.

Furthermore, in the measurement device 10' of this embodiment, fluid drive units 41a, 41b, 42a and 42b connected to the flow pass switchers 38, respectively, are provided. As the fluid drive units 41a, 41b, 42a and 42b, for example, pumps, air compressors, syringes, or the like are used.

Moreover, in the measurement device 10', the current application section 18 and the measurement section 33 can be switched by multiplexers 36 and 37. The operations of the current application section 18, the measurement section 33 and the multiplexers 36 and 37 are controlled by the calculator 35.

With the measurement device 10' of this embodiment, multiple measurements can be performed at a time.

Embodiment 4

Figure 10:
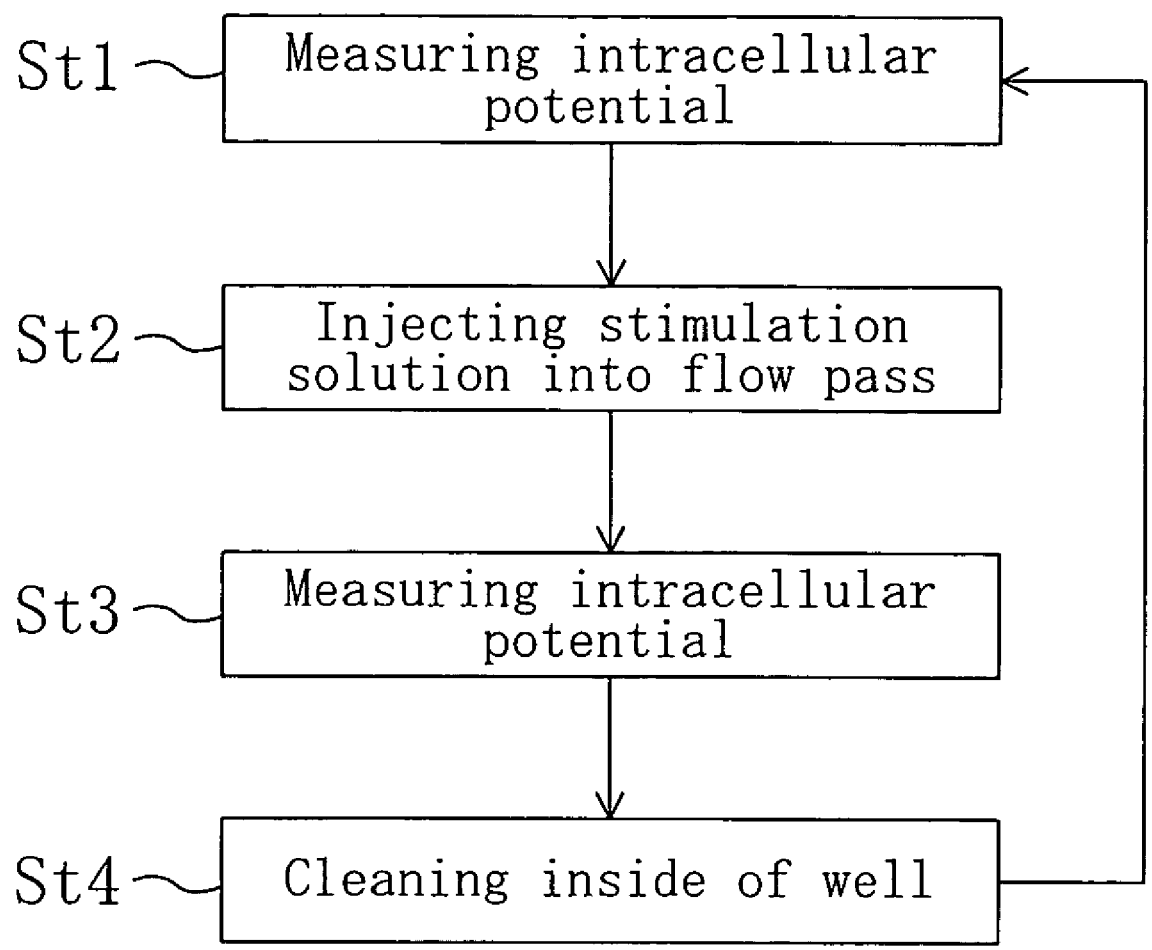
FIG. 10 is a flow chart illustrating a measurement method according to EMBODIMENT 4 of the present invention.

In this embodiment, a measurement method performed using the measurement device 10 of EMBODIMENT 1 will be described with reference to FIG. 10. FIG. 10 is a flow chart describing the measurement method of this embodiment.

First, as shown in FIG. 10, in Step St1, after the cell 21 has been introduced into the well 19 by the method using the laminar flow described in EMBODIMENT 1 and the position of the cell 21 has been controlled and fixed to the microelectrode 11, an intracellular potential is measured.

Next, as shown in FIG. 10, in Step St2, the valve V is switched so that a stimulating solution is injected from the inlet connector 13 into the flow pass 9. When the stimulating solution reaches the well 19, the injection of the stimulating solution is stopped to stop the flow of a liquid in the flow pass 9. Thus, the stimulating solution is diffused in the well 19 to stimulate the cell 21 fixed to the microelectrode 11.

Next, as shown in FIG. 10, in Step St3, the intracellular potential is measured again.

Next, as shown in FIG. 10, in Step St4, the inside of the well 19 is cleaned. Specifically, the valve V is switched so that a cleansing liquid is injected from the inlet connector 13 into the flow pass 9. When the cleansing liquid reaches the well 19, the injection of the cleansing liquid is stopped. Thus, the cleansing liquid is diffused in the well 19. Subsequently, the cleansing liquid is exhausted from the outlet connector 14. Specifically, in this step, the operations of injecting the cleansing liquid and exhausting the cleansing liquid are repeated. Thus, the well 19 is cleaned.

Next, as shown in FIG. 10, Steps St1 through St4 are repeated as the concentration of the stimulator contained in the stimulating solution is gradually increased. Thus, the correlation between the concentration of the stimulator and the intracellular potential can be examined.

Moreover, by introducing an antagonist into the well 9 in the same manner as introduction of the stimulator before Step St2, the correlation between the antagonist and the intracellular potential can be examined.

Examples of the present invention will be described hereinafter. The following examples are described for the purposed of emplifying the present invention and do not limit the present invention.

EXAMPLES

Hereinafter, examples of measurement of an isolated cell as a biological sample using the measurement device 10 of EMBODIMENT 1 will be described.

Example 1

Fabrication of Measurement Device

A glass plate having a thickness of 2 mm was used as a material for a substrate 16. On a surface of the grass plate measuring 60 mm wide by 100 mm long, a concave portion 9a was formed so as to have a width of 150 μm, a length of 3 mm and a depth of 70 μm using a ø100 μm end mill. Thereafter, the concave portion 9a was carefully polished. A through hole having a diameter of 1.5 mm serving as an inlet or an outlet was formed in each of end portions of the concave portion 9a.

A single crystalline silicon wafer was used as a material for a substrate 17. On a surface of the substrate 17, by photolithography and anisotropic etching, formed were a well 19 having an inverted trapezoid shape, a width of 150 μm, a length of 500 μm and a depth of 30 μm, resistance baths 6a and 6b each having an inverted trapezoid shape, a width of 400 μm, a length of 1000 μm and a depth of 30 μm, and communicating tubes 15a and 15b each having an inverted triangular prism shape, a width of 10 μm, a length of 500 μm and a depth of 7.1 μm. Specific fabrication process steps are as follows.

After having been baked at 120° C. for 20 minutes, the single crystalline wafer was sufficiently dried and then spin coating was performed at 1000 rpm for 5 seconds to form a photoresist over a surface of the single crystalline silicon wafer. Thereafter, the substrate was pre-baked at 90° C. for 10 minutes. The well was then mask-patterned by exposure, developed and cleaned using a developer for exclusive use in patterning, and wet-etched to complete the well 19, the resistance baths 6a and 6b and the communicating tubes 15a and 15b. In this case, a mixed solution of 24 wt % KOH and IPA (isopropyl alcohol) as a surfactant was used as an etchant. The mixed solution was circulated using a pump and the temperature of the solution was controlled to be 73° C.±3° C. Under this condition, etching was performed for 35 minutes.

A microelectrode 1 was formed by performing under etching directly under a circular etching mask using a single crystalline silicon as a material. The microelectrode having an approximately cone shape with a sharp tip, a concave outer surface, a tip neighborhood diameter of about 1 μm, a bottom surface portion with a 16 μm diameter, and a height of about 8 μm was obtained. Thereafter, the surface of the microelectrode was subjected to sputtering to dispose a tungsten film thereon, and then the electrode was coated with polyimide, except for the tip, to provide an insulation.

Thereafter, thin film resistors 3a and 3b and respective lead interconnects thereof, a reference electrode 2 and a lead interconnect thereof, and a lead interconnect from the microelectrode 1 were formed on the substrate 17. To describe simply, a platinum film of a thickness of 0.5 μm was formed over the substrate 17 by a vacuum deposition method. And then, other part of the platinum film than part thereof in which the electrode, resistors and interconnects were located was removed. Note that each of the interconnects had a width of 80 μm and each of the thin film resistors 3a and 3b had a comb shape having a width of 25 μm.

Then, the substrate 16 and the substrate 17 were bonded to each other by anodic bonding to form a closed flow pass 9. Anodic bonding was performed with a direct voltage of 600 V applied at a temperature of 400-600° C. for 10 minutes.

Thereafter, an inlet connector 13 and an outlet connector 14 were connected to the through holes, respectively, each being formed in each of both ends of the concave portion 9a of the substrate 16. Subsequently, a compressor was connected to the connector connected to the outlet of the flow pass 9 via a three-way cock and a fitting joint.

Example 2

Measurement of the Action Potential of a Nerve Cell

Pressure in part of the flow pass 9 of the measurement device 10 located closer to the outlet connector 14 was reduced to be a slightly lower pressure than an atmosphere pressure, and then culture medium (40 mM NaCl, 1.7 mM KCl, 4.1 mM $CaCl_2$, 1.5 mM $MgCl_2$, 5 mM glucose, 5 mM HEPES, pH 7.9) for lymnaea stagnalis was injected into the flow pass 9 from the inlet connector 13 at a flow rate of 10-100 μl/min using a peristaltic pump connected to the inlet connector 13. At this time, it was observed that the medium flew into the resistance baths 6a and 6b through the communicating tubes 15a and 15b.

Then, after having confirmed that the lymnaea stagnalis medium was injected to fill the outlet connector 14, the operation of reducing pressure by suction from the outlet connector 14 was stopped and the three-way cock was opened to return the pressure in the part to the atmosphere pressure. At this time, the medium further flew into the communicating tubes 15a and 15b, so that a vapor-liquid interface was located in each of a connection portion between the communicating tube 15a and the resistance bath 6a and a connection between the communicating tube 15b and the resistance bath 6b.

A ganglion taken from lymnaea stagnalis was shaken in a 1 mg/ml protease type 14 (SIGMA, P-5147) solution at 37° C. for 25 minutes to isolate a nerve cell. The obtained nerve cell of the lymnaea stagnalis was suspended into the lymnaea stagnalis medium and then carefully introduced into the flow pass 9 from the inlet connector 13. The flow pass 9 was then observed under a microscope. When the valve V connected to the inlet connector 13 and the outlet connector 14 was closed at the moment when the lymnaea stagnalis nerve cell reached an upper portion of the well 19, introduction of the nerve cell into the well 19 was confirmed.

Subsequently, when a current of 10 mA p-p (mili-ampere peak to peak) was applied to each of the thin film resistors 3a and 3b for 30 seconds, the nerve cell moved in the well 19 to be inserted into the microelectrode 1. At this time, a rectangular wave current stimulation pulse of 10 nA p-p was applied to the microelectrode 1 for 1 ms and an intracellular potential was measured by a voltage clamp method. The intracellular potential was recorded for 60 times at intervals of 310 seconds and with a sampling frequency of 50 kHz.

Figure 11:
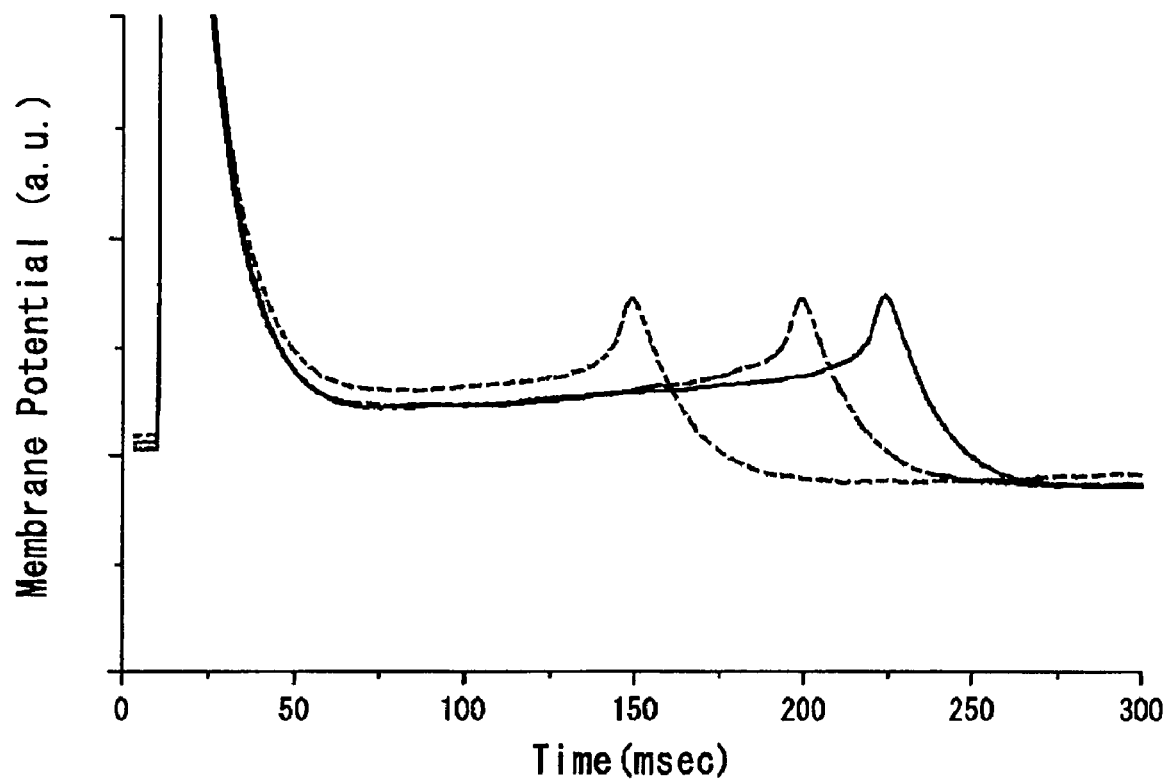
FIG. 11 is a graph showing the action potential of a nerve cell of lymnaea stagnalis when current stimulation was applied to the cell, measured using the measurement device of EMBODIMENT 1.

Next, measurement was performed by applying current stimulation, i.e., a rectangular current pulse of 8 nA p-p for 1 ms. Results of three measurements are shown in FIG. 11. Note that in all of the measurements in this example, bridge balance was taken and capacitance compensation of a device was performed. Moreover, a structure was made so that measurement data passed through a 5 kHz, 4th Butterworth type low-pass filter, and then input into a calculator.

As shown in FIG. 11, a potential response of the cell due to current stimulation was observed in a period between 150 ms and 250 ms and it was shown that the action potential of a cell can be detected by the method of this embodiment in the same manner as in a known intracellular recording method.

Example 3

As the biological sample 21, rat artery smooth muscles (SM) were used. As a solution to be injected into the measurement device 10, DMEM culture medium to which 10% FBS (fetal bovine serum) was added was used. An SM cell was inserted into the microelectrode 1 by performing the same operation as that of EXAMPLE 2, and then an intracellular potential when 100 μM carbachol, which was an analog of acetylcholine, was introduced as a solution was measured by a voltage clamp method.

Figure 12:
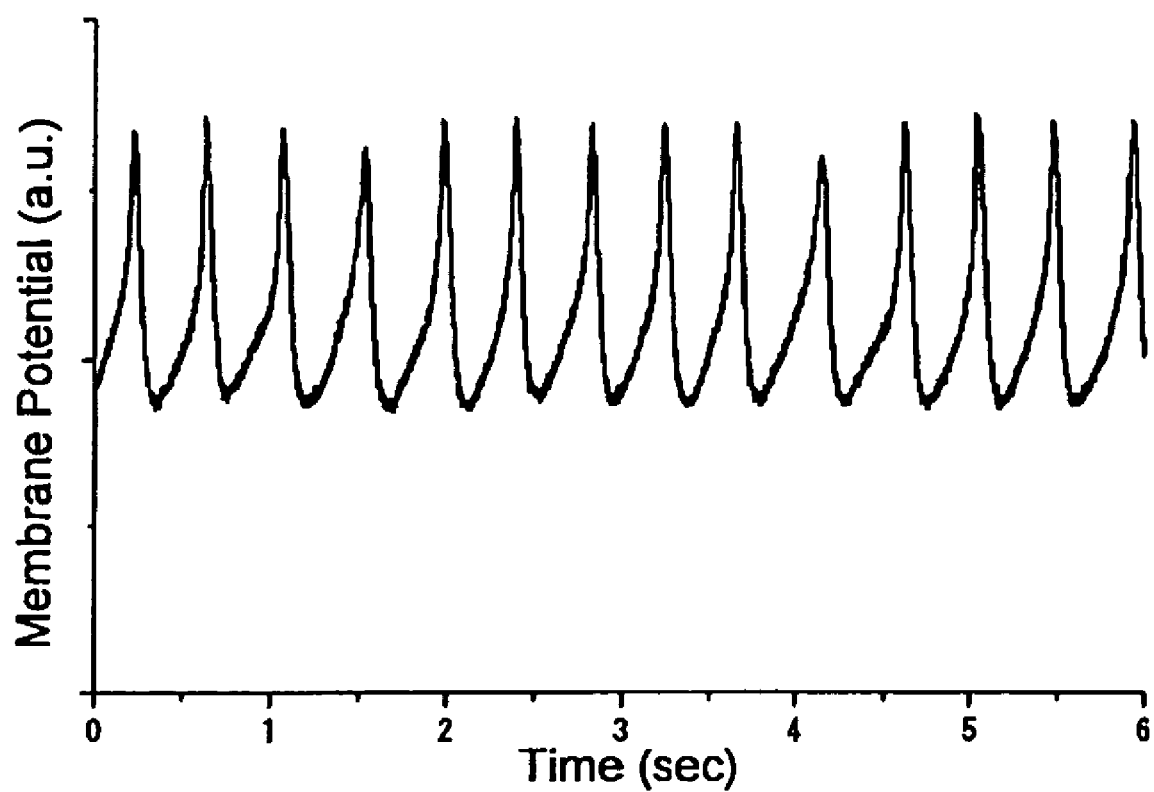
FIG. 12 is a graph showing the action potential of an artery smooth muscle cell when carbachol was added to the cell, measured using the measurement device of EMBODIMENT 1.

Results of measurement of the spontaneous action potential obtained when carbachol was administered are shown in FIG. 12. As shown in FIG. 12, the action potential in response to carbachol was detected. The results were similar to those obtained by the known intracellular recording method.

Figure 13:
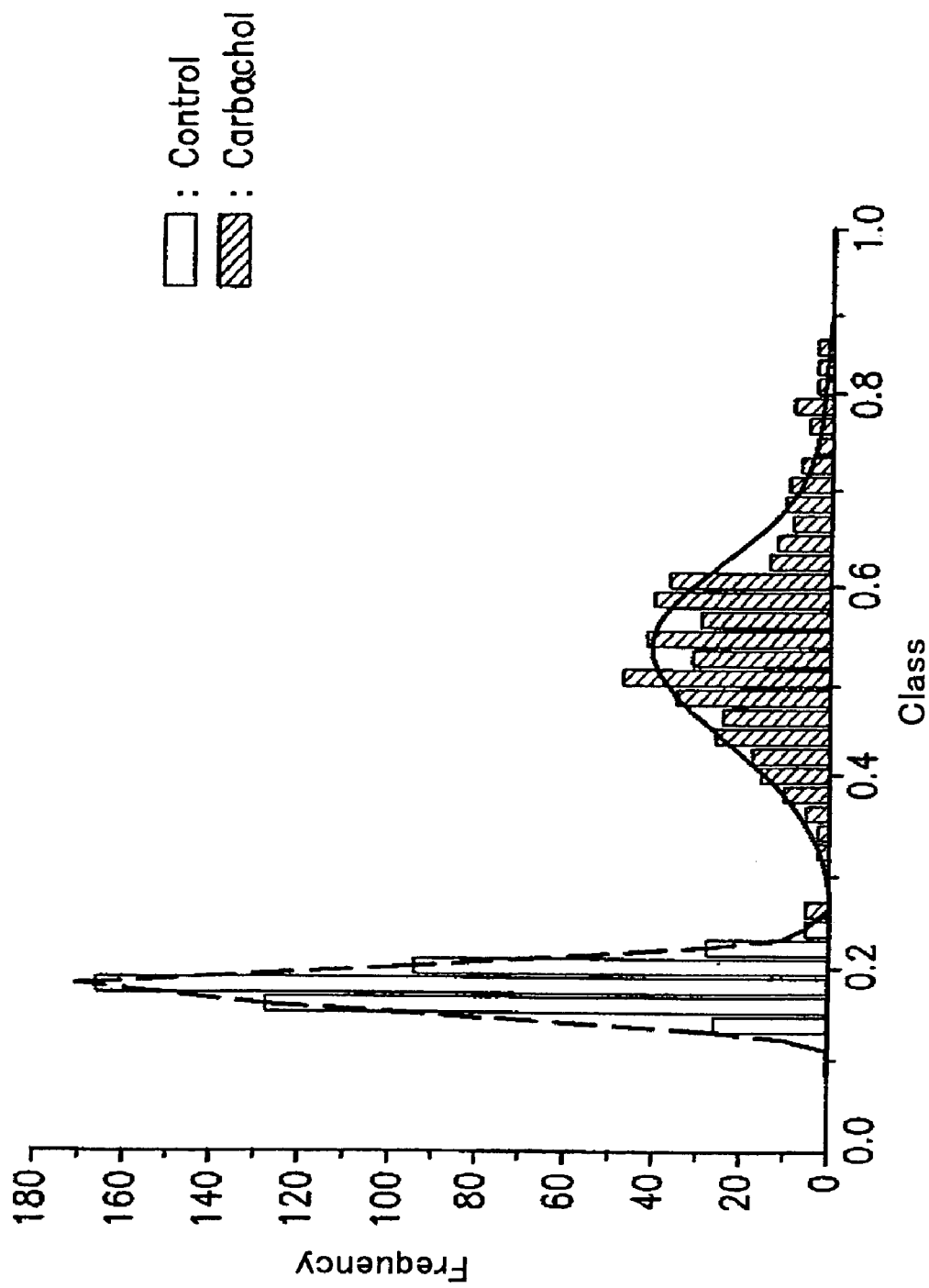
FIG. 13 is a histogram of standard deviation per 10 ms for the action potential of an artery smooth muscle cell when carbachol was added to the cell, measured using the measurement device of EMBODIMENT 1.

Furthermore, FIG. 13 shows a histogram of standard deviation per 10 ms for data obtained by signal-processing data obtained by the known intracellular recording method. FIG. 13 is a histogram of standard deviation per 10 ms before and after a carbachol administration. The mean value and half width of the graph, obtained by approximating the histogram before and after a carbachol administration with a normal distribution are 0.185 and 0.04, respectively, before the administration and 0.545 and 0.21, respectively, after the administration. This shows that the mean value of the standard deviation per 10 ms was increased after the administration of carcachol. The reason for the increase was that by the administration of carbachol, ion channels of the lymnaea stagnalis nerve cell was activated, and changes in conductance due to switching of the activated ion channels is expressed by voltage change. From FIG. 13, it was confirmed that with the measurement device 10, ion channel properties for a nerve stimulator can be determined as in the same manner in the known intracellular recording method.

In this manner, with the measurement device 10, it is possible to measure the action of a cell according to switching of a channel in a simple manner by an ion channel activation degree extracting method without performing the known intracellular recording method. Accordingly, by comparing, using the measurement device 10, absolute values of channel activation degrees before and after drug administration to a cell or for an administration dosage, or increase and decrease in the channel activation degrees, measurement of cell channel activation degrees and qualitative and quantitative classification of effects of a drug can be performed.

It can be seen from the results obtained in EXAMPLE 2 and EXAMPLE 3 that the measurement device 10 can high-sensitively obtain by the microelectrode 1 a cell membrane potential and a temporary action potential from the cell 21 lead by the microelectrode 1.

As has been described, according to the present invention, a measurement device which allows electrophysiological evaluation of a biological sample to be performed in a simple, accurate, high-speed and automatic manner can be provided.

INDUSTRIAL APPLICABILITY

Measurement device and method according to the present invention is used for performing electrophysiological evaluation of a biological sample, represented by chemical screening and the like.

The invention claimed is:

1. A measurement device for measuring an electric signal from a biological sample, comprising:
   a first substrate; and
   a second substrate formed on the first substrate,
   wherein the second substrate includes a concave portion thereby forming a flow pass between the first substrate and the second substrate,
   wherein the flow pass is configured to have a first end and second end, and wherein said flow pass extends in a first direction, from said first end to said second end;
   a pair of introduction orifices connected to both ends of the flow pass, respectively;
   a concave well positioned in the flow pass;
   a reference electrode positioned in the flow pass;
   at least a microelectrode formed in the well and configured to measure an electric signal from the biological sample;
   a first communicating tube connected to a first portion of the well and extending in a second direction;
   a second communicating tube connected to a second portion of the well and extending in a third direction;
   first and second resistance baths connected to the first and second tubes, respectively; and
   first and second resistors arranged in the first and second communicating tubes, respectively, or the first and second resistance baths, respectively.

2. The measurement device of claim 1, wherein the first and second communicating tubes are arranged so as to have line-symmetry with respect to the flow pass.

3. The measurement device of claim 1, wherein the first and second communicating tubes are arranged so that a straight line extending along the first communicating tube and a straight line extending along the second communicating tube intersect with each other toward said at least a microelectrode.

4. The measurement device of claim 1, wherein said at least a microelectrode includes a protruding end portion.

5. The measurement device of claim 1, wherein said at least a microelectrode is provided plural in number.

6. The measurement device of claim 5, wherein a surface area of the reference electrode is larger than a total surface area of the plurality of microelectrodes.

7. The measurement device of claim 1,
   wherein the first substrate includes the well, the reference electrode, the microelectrode, the first and second communicating tubes, the first and second resistance baths, and the first and second resistors, and
   wherein the second substrate includes cavities which serve as the pair of introduction orifices when the second substrate is provided on the first substrate and are formed in both ends of the concave portion, respectively.

8. The measurement device of claim 7, wherein the second substrate is formed of a transparent material.

9. The measurement device of claim 7, wherein the first substrate is formed of a semiconductor material.

10. The measurement device of claim 1, wherein a volume of the first communicating tube is smaller than one fifth of a volume of the first resistance bath, and
    wherein a volume of the second communicating tube is smaller than one fifth of a volume of the second resistance bath.

11. The measurement device of claim 1, wherein a surface of the flow pass has been subjected to hydrophilic processing.

12. The measurement device of claim 1, wherein each of the first and second resistors has a comb shape.

13. The measurement device of claim 3, further comprising:
    a third communicating tube connected to a third part of the well and extending in a fourth direction;
    a third resistance bath connected to the third communicating tube; and
    a third resistor arranged in the third communicating tube or the third resistance bath.

14. The measurement device of claim 13, wherein the first and second communicating tubes are arranged so that a line extending along each said tubes extends toward said at least a microelectrode comprising a first and second end and each said tubes has an opening toward said at least a microelectrode, and
- wherein the third communicating tube is arranged so that the first end portion of said at least a microelectrode is located substantially on a straight line extending along the third communicating tube.

15. The measurement device of claim 1,
- wherein the second substrate further comprises a second concave portion which serves as a second flow pass between the first substrate and the second substrate;
- wherein the second flow pass is configured to have a first end and a second end, and
- wherein said second flow pass extends in the first direction;
- another pair of introduction orifices connected to both ends of said second flow pass, respectively;
- a second concave well formed in said second flow pass;
- a second reference electrode formed in said second flow pass;
- at least a second microelectrode formed in said second well and configured to measure a second electric signal from the biological sample;
- a fourth communicating tube connected to a first portion of said second well and extending in the second direction
- a fifth communicating tube connected to a second portion of said second well;
- a third resistance bath and a fourth resistance bath connected to said fourth and fifth communicating tubes, respectively; and
- a third resistor and a fourth resistor arranged in said fourth and fifth communicating tubes, respectively, or in said third and fourth resistance baths, respectively.

16. A measurement method for measuring an electrical signal from a biological sample, the method comprising the steps of:
- a) preparing a measurement device comprising:
- a first substrate; and
- a second substrate formed on the first substrate,
- wherein the second substrate includes a concave portion thereby forming a flow pass between the first substrate and the second substrate,
- wherein the flow pass is configured to have a first end and second end, and wherein said flow pass extends in a first direction, from said first end to said second end;
- a pair of introduction orifices connected to both ends of the flow pass, respectively;
- a concave well positioned in the flow pass;
- a reference electrode positioned in the flow pass;
- at least a microelectrode formed in the well and configured to measure an electric signal from the biological sample;
- a first communicating tube connected to a first portion of the well and extending in a second direction;
- a second communicating tube connected to a second portion of the well and extending in a third direction;
- first and second resistance baths connected to the first and second tubes, respectively; and
- first and second resistors arranged in the and second communicating tubes, respectively, or the first and second resistance baths, respectively
- b) introducing an electrolyte solution into the flow pass by reduction of a pressure in the flow pass to fill the flow pass;
- c) returning the pressure in the flow pass to an atmosphere pressure;
- d) arranging the biological sample in the well;
- e) closing up the flow pass;
- f) applying a current to the first or second resistor to bring said at least a microelectrode in contact with the biological sample; and
- g) measuring an electrical signal from the biological sample.

17. The measurement method of claim 16, further comprising after the step f), the step h) of applying an electrical pulse to said at least a microelectrode.

18. The measurement method of claim 16 or 17, further comprising the step i) of administering a drug from one of the pair of introduction orifices.

* * * * *

UNITED STATES PATENT AND TRADEMARK OFFICE
CERTIFICATE OF CORRECTION

| | | |
|---|---|---|
| PATENT NO. | : 7,462,324 B2 | Page 1 of 1 |
| APPLICATION NO. | : 10/495621 | |
| DATED | : December 9, 2008 | |
| INVENTOR(S) | : Nobuhiko Ozaki et al. | |

It is certified that error appears in the above-identified patent and that said Letters Patent is hereby corrected as shown below:

ON THE TITLE PAGE:

In Item "(87) PCT Pub. Date:" change "May 5, 2003" to --May 30, 2003--;

In Item "(30) Foreign Application Priority Data", change "Nov. 19, 2002" to --Nov. 19, 2001--;

In Item "(57) Abstract", in the second line, change "11 includes a substrates 17" to --11 includes a substrate 17--.

IN THE CLAIMS:

In Column 21, Line 23, change "mieroelectrode" to --microelectrode--; and

In Column 22, Line 19, change "arranged in the and second" to --arranged in the first and second--.

Signed and Sealed this

Twenty-sixth Day of May, 2009

JOHN DOLL
*Acting Director of the United States Patent and Trademark Office*